United States Patent
Douglas

(10) Patent No.: US 11,986,345 B2
(45) Date of Patent: May 21, 2024

(54) REPRESENTATION OF A TARGET DURING AIMING OF AN ULTRASOUND PROBE

(71) Applicant: Verathon Inc., Bothell, WA (US)

(72) Inventor: Marion Douglas, Snohomish, WA (US)

(73) Assignee: Verathon Inc., Bothell, WA (US)

( * ) Notice: Subject to any disclaimer, the term of this patent is extended or adjusted under 35 U.S.C. 154(b) by 0 days.

(21) Appl. No.: 16/926,055

(22) Filed: Jul. 10, 2020

(65) Prior Publication Data

US 2021/0007710 A1    Jan. 14, 2021

Related U.S. Application Data

(60) Provisional application No. 62/873,564, filed on Jul. 12, 2019.

(51) Int. Cl.
| | |
|---|---|
| A61B 8/00 | (2006.01) |
| A61B 8/08 | (2006.01) |
| A61B 8/14 | (2006.01) |
| G06N 3/02 | (2006.01) |

(52) U.S. Cl.
CPC ............ *A61B 8/4245* (2013.01); *A61B 8/085* (2013.01); *A61B 8/14* (2013.01); *A61B 8/461* (2013.01); *A61B 8/469* (2013.01); *A61B 8/483* (2013.01); *A61B 8/5207* (2013.01); *A61B 8/54* (2013.01); *G06N 3/02* (2013.01)

(58) Field of Classification Search
None
See application file for complete search history.

(56) References Cited

U.S. PATENT DOCUMENTS

| | | | |
|---|---|---|---|
| 5,645,066 A | | 7/1997 | Gandini et al. |
| 6,360,116 B1 | * | 3/2002 | Jackson, Jr. ......... A61N 5/1027 |
| | | | 600/427 |
| 10,194,990 B2 | | 2/2019 | Amanatullah et al. |
| 11,311,269 B2 | * | 4/2022 | Dunbar .................. A61B 8/463 |

(Continued)

FOREIGN PATENT DOCUMENTS

| | | |
|---|---|---|
| KR | 10-2018-0005812 A | 1/2018 |
| WO | 2017/186610 A1 | 11/2017 |
| WO | 2018/209193 A1 | 11/2018 |

OTHER PUBLICATIONS

PCT International Search Report and Written Opinion issued for the corresponding international application No. PCT/US2020/041607 dated Oct. 20, 2020, 11 pages.

*Primary Examiner* — Patrick Fernandes
*Assistant Examiner* — Nicholas A Robinson
(74) *Attorney, Agent, or Firm* — Snyder, Clark, Lesch & Chung, LLP

(57) ABSTRACT

A system may include an ultrasound probe and a controller unit configured to communicate with the ultrasound probe. The controller unit may be further configured to select an aiming mode for an ultrasound probe; detect a target of interest; determine a centroid for the detected target of interest; display a center indicator based on the determined centroid; detect that the center indicator is within a threshold number of pixels or distance of a centerline of a field of view of the ultrasound probe; and highlight the generated center indicator, in response to detecting that the center indicator is within the threshold number of pixels or distance of the centerline.

23 Claims, 17 Drawing Sheets

(56) References Cited

U.S. PATENT DOCUMENTS

| | | | |
|---|---|---|---|
| 2002/0087080 A1* | 7/2002 | Slayton | A61B 8/42 |
| | | | 600/459 |
| 2004/0138559 A1* | 7/2004 | Cheng | A61B 8/465 |
| | | | 128/916 |
| 2004/0267123 A1 | 12/2004 | McMorrow et al. | |
| 2009/0264757 A1 | 10/2009 | Yang et al. | |
| 2010/0069756 A1 | 3/2010 | Ogasawara et al. | |
| 2012/0237102 A1* | 9/2012 | Savitsky | G09B 23/286 |
| | | | 382/131 |
| 2012/0296214 A1 | 11/2012 | Urabe et al. | |
| 2014/0364720 A1 | 12/2014 | Darrow et al. | |
| 2015/0154890 A1* | 6/2015 | Savitsky | G09B 23/286 |
| | | | 434/262 |
| 2016/0220316 A1 | 8/2016 | Paon et al. | |
| 2017/0312031 A1 | 11/2017 | Amanatullah et al. | |
| 2017/0312032 A1 | 11/2017 | Amanatullah et al. | |
| 2018/0330518 A1* | 11/2018 | Choi | A61B 8/42 |
| 2019/0015076 A1 | 1/2019 | Rouet et al. | |
| 2019/0117999 A1 | 4/2019 | Fontanarosa et al. | |
| 2019/0125301 A1 | 5/2019 | Jago et al. | |
| 2019/0209119 A1 | 7/2019 | Mauldin, Jr. et al. | |
| 2020/0113544 A1* | 4/2020 | Huepf | G06T 7/0012 |
| 2022/0031489 A1* | 2/2022 | Calzi | A61B 5/07 |

\* cited by examiner

REPRESENTATION OF A TARGET DURING AIMING OF AN ULTRASOUND PROBE

PRIORITY INFORMATION

This patent application claims benefit of priority to U.S. Provisional Application No. 62/873,564, entitled "REPRESENTATION OF A TARGET DURING AIMING OF AN ULTRASOUND PROBE" and filed on Jul. 12, 2019, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. In order for a user to properly scan a target organ/structure, the user may need to place the ultrasound probe in a particular position with respect to the target organ/structure. Correct placement of the ultrasound probe may present various challenges.

DETAILED DESCRIPTION OF PREFERRED EMBODIMENTS

Figure 1A:
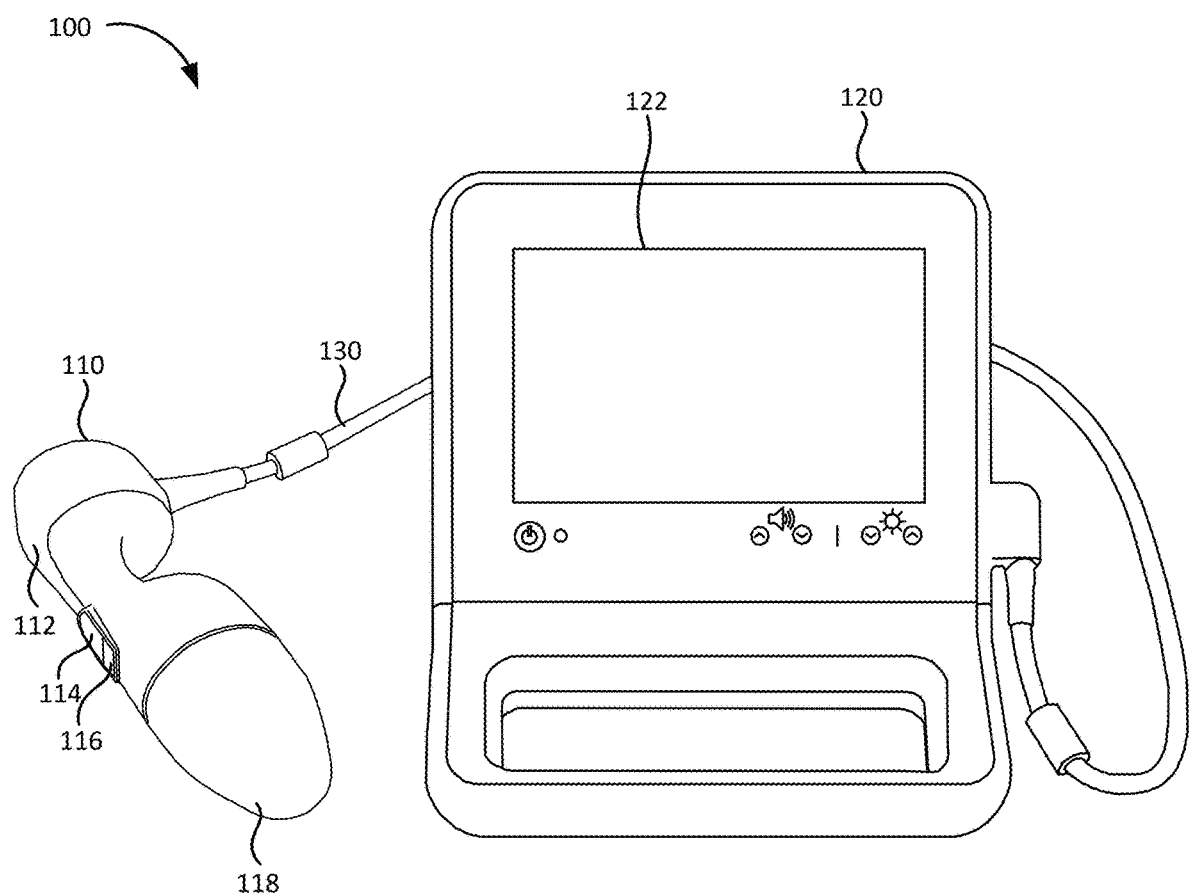
FIG. 1A is a diagram illustrating an exemplary ultrasound system according to an implementation described herein.

The following detailed description refers to the accompanying drawings. The same reference numbers in different drawings identify the same or similar elements.

An ultrasound probe may be positioned on a patient's body to perform a three-dimensional (3D) scan of a target of interest, such as a body organ, joint, blood vessel, and/or another type of area of a patient's body. A 3D scan may include a set of ultrasound images, such as, for example, B-mode images, captured in different planes transecting the target or area of interest. For example, a 3D scan may include B-mode images taken at particular angular intervals in a circle around a center of the target of interest. The 3D scan may be used to characterize the target of interest. For example, a 3D scan of a bladder may be used to determine the volume of fluid inside the bladder and the volume may be used to select a medical intervention, such as catheterizing the bladder.

Before the 3D scan is taken, the ultrasound probe may need to be accurately positioned over the area of interest. For example, in many situations, a target of interest may have cross-sections that significantly differ in size in different planes. If the ultrasound probe is not centered and positioned in the correct direction, clipping of the target of interest may occur during the 3D scan. In other words, parts of the target or area of interest may be omitted from the 3D scan, wasting time and resources.

In order to position the ultrasound probe, a user may select an aiming mode for the ultrasound probe. During the aiming mode, the ultrasound probe may repeatedly perform a scan in a particular plane to obtain a cross-section of the target or area of interest in the particular plane. A user may move the ultrasound probe to more accurately position the ultrasound probe based on ultrasound images obtained and displayed while the ultrasound probe is in the aiming mode.

However, displaying ultrasound images during the aiming mode may not be desirable. For example, a user may not be trained to interpret ultrasound images to make a diagnosis and yet may be tempted to interpret ultrasound images displayed during the aiming mode. Therefore, a provider of medical services may require that ultrasound images not be displayed while an ultrasound probe is used to characterize a target of interest (e.g., to obtain a fluid volume measurement). However, the user may still need feedback information from the ultrasound probe in order to accurately position the ultrasound probe during aiming.

Implementations described herein relate to representation of a target during aiming of an ultrasound probe or another type of device using a different imaging modality. Thus, rather than displaying an obtained ultrasound image of a target of interest during aiming of an ultrasound probe, an ultrasound system may display a symbolic or pictographic representation of the target to indicate to the user the alignment of the ultrasound probe with the target. During aiming of the ultrasound probe, the ultrasound probe may need to be centered with respect to the target of interest and aligned in order to capture an ultrasound image in which the cross-sectional area of the target of interest is maximized. Therefore, the symbolic or pictographic representation may include a center indicator to indicate the center of the target of interest with respect to the ultrasound probe and an area indicator to represent the target of interest and provide information to the user as to whether a maximum area of the target of interest has been identified.

When the center indicator is aligned with the centerline of the field of view of the ultrasound probe, the center indicator may be highlighted. The user may then be instructed to tilt the ultrasound probe (e.g., cranially and caudally) to find the maximum cross-sectional area for the target of interest. When the maximum cross-sectional area for the target is identified and the probe position is aligned to capture ultrasound images of the target at the identified maximum cross-sectional area, the area indicator may be highlighted. After the center indicator and the area indicator are highlighted, the ultrasound probe may exit the aiming mode and initiate a 3D scan of the target.

The symbolic or pictographic representation of the target may be selected and displayed to minimize the likelihood of the user using the displayed symbolic or pictographic representation for diagnostic purposes while the ultrasound system is in an aiming mode. For example, while the ultrasound system may track the size of the target of interest in an obtained ultrasound image as the position of the ultrasound probe changes, the size of the displayed area indicator may remain the same size and not change to reflect the detected change in the size of the target.

Thus, an ultrasound system may be configured to select an aiming mode for an ultrasound probe; detect a target of interest; determine a centroid for the detected target of interest; display a center indicator based on the determined centroid; detect that the center indicator is within a threshold number of pixels or distance of a centerline of a field of view of the ultrasound probe; and highlight the generated center indicator, in response to detecting that the center indicator is within the threshold number of pixels or distance of the centerline.

The ultrasound system may be further configured to display an area indicator based on the determined area; determine an area for the detected target of interest; and track the area for the detected target of interest, wherein the displayed area indicator does not change in size as the tracked area for the detected target of interest changes. The ultrasound system may determine that a current area corresponds to a maximum area and highlight the displayed area indicator, in response to determining that the current area corresponds to the maximum area.

Determining that the current area corresponds to the maximum area may be based on the current area increasing and decreasing a particular number of times as the user moves the ultrasound probe back and forth across a position that is aligned to capture ultrasound images of the target at the identified maximum cross-sectional area. The ultrasound system may be further configured to determine that the ultrasound probe has remained centered and positioned pointing at the maximum area for at least a particular time period and exit the aiming mode and initiating a 3D scan of the target of interest, in respond to determining that the ultrasound probe has remained centered and positioned pointing at the maximum area for at least the particular time period.

Detecting the target of interest may include using a neural network to identify boundaries of the target of interest. Determining whether the detected target of interest is centered may include representing the boundaries as a polygon with a set of vertices and computing the centroid based on a sum of the differences in the coordinates of adjacent vertices divided by the area of the polygon. In other implementations, determination of whether the detected target of interest is centered may be computed based on a center between a left-most vertex and a right-most vertex of the plurality of vertices in order to take into account targets with unusual shapes.

In some implementations, rather than determining a centroid for the detected target of interest and displaying a center indicator based on the determined centroid, it may be advantageous to align the ultrasound probe along an edge of the target of interest or along an edge of another structure.

Furthermore, in some implementations, the aiming visual cues may be augmented by audible and/or haptic feedback. For example, when the ultrasound probe is centered and the conditions for highlighting the center indicator are satisfied, a first audible sound (e.g., a ping or beep sound, a recorded voice announcing "probe is centered", etc.) may be generated by the ultrasound system. Additionally, the ultrasound probe may vibrate in a first pattern using a vibration motor included in the ultrasound probe. Similarly, when the maximum area of the target is determined and the conditions for highlighting the area indicator are satisfied, the ultrasound system may generate a second sound (e.g., a different type of ping or beep sound, a recorded voice announcing "maximum area identified", etc.) and/or the ultrasound probe may vibrate in a second pattern using the vibration motor.

In some implementations, the symbolic or pictographic representation of the target, represented by the center indicator and the area indicator, may be displayed in a B-mode view associated with the ultrasound probe and using the ultrasound probe as the frame of reference, in which the position of the ultrasound probe is stationary and in which the center indicator and/or area indicator is moved in the B-mode view when the ultrasound probe is moved. In other implementations, the symbolic or pictographic representation of the target, represented by the center indicator and the area indicator, may be displayed along with a representation of the patient's body and using the patient's body as the frame of reference, in which the patient's body is stationary and in which the field of view of the ultrasound probe is moved when the ultrasound probe is moved. The patient's body may be displayed in a transverse plane view, in a sagittal plane view, and/or in another type of view. The user may be able to switch the view between different planes.

In some implementations, the ultrasound images captured while in aiming mode and/or during a 3D scan may correspond to B-mode ultrasound images. In other implementations, other types of ultrasound images may be used during the aiming mode and the aiming mode may be followed by other types of images additionally or alternatively to a 3D scan. As an example, the ultrasound system may utilize probability mode (P-mode) ultrasound images. A P-mode ultrasound image may correspond to an ultrasound image (e.g., a B-mode ultrasound image, etc.) in which each particular pixel is mapped to a probability indicating whether that particular pixel is within or part of a target organ/structure.

As another example, the ultrasound system may utilize segmentation map ultrasound images. A segmentation map ultrasound image may correspond to an ultrasound image with segmentation processing performed on captured ultrasound data. For example, in a segmentation map ultrasound image, different body structures may be displayed in different colors (e.g., bladder in yellow, background tissues in gray, etc.). As yet another example, the ultrasound system may utilize Doppler mode ultrasound images (e.g., Power Doppler, Continuous Wave Doppler, Pulsed Wave Doppler, etc.), harmonic mode ultrasound images, motion mode (M-mode) ultrasound images, and/or any other type of imaging modality that uses ultrasound data while in the aiming mode. Moreover, the 3D scan may be performed using P-mode ultrasound images, Doppler mode ultrasound images, harmonic mode ultrasound images, M-mode ultrasound images, and/or any other type of imaging modality that uses ultrasound data.

In some implementations, the ultrasound system may utilize an aiming mode that uses multiple B-mode images in different planes (e.g., 4 planes at 45° to each other, 12 planes at 15° to each other, etc.). Such a scanning mode may be referred to as a C-mode. The ultrasound system may scan the multiple B-mode images in different planes and construct a top-down view of an area of interest (e.g., in a frontal/coronal plane of the patient's body) and generate a symbolic or pictographic representation of the target. Furthermore, the ultrasound system may generate a symbolic representation of the field of view of the ultrasound probe. For example, the ultrasound system may generate an oval shape representing a cross-section of the field of view of the ultrasound probe with respect to the target, analogous to a beam of a flashlight shined onto a surface. Such a representation of the field of view may be referred to as a flashlight view of the ultrasound probe. The user may then be directed to position the ultrasound probe to align the symbolic or pictographic representation of the target in the middle of the flashlight beam representation. When the symbolic or pictographic representation of the target is aligned with the ultrasound probe beam representation, the symbolic or pictographic representation of the target may be highlighted and the user may be directed to perform the scan.

In some implementations, the aiming mode may be followed by other types of processing additionally or alternatively to a 3D scan. As an example, the aiming mode may be used in connection with positioning a needle guide for needle insertion (e.g., to obtain a biopsy sample, etc.). As another example, the aiming mode may be used to position the ultrasound robe to measure the volume of an area of interest (e.g., bladder volume measurement, prostate volume measurement, uterus volume measurement, aorta size measurement, etc.).

While particular implementations described herein relate to representation of a target during aiming of an ultrasound probe, in other implementations, the representation of the target may be generated while aiming an instrument or device that uses a different type of imaging modality. For example, in other implementations, the representation of the target may be generated while aiming an optical camera, a camera for capturing three-dimensional (3D) images, a thermal camera, an infrared (IR) camera, a functional near-infrared spectroscopy (fNIRS) imaging device, a magnetic resonance imaging (MRI) device, an x-ray imaging device, and/or another type of imaging device.

FIG. 1A is a diagram illustrating an exemplary ultrasound system 100 according to an implementation described herein. As shown in FIG. 1A, ultrasound system 100 may include an ultrasound probe 110, a base unit 120, and a cable 130.

Ultrasound probe 110 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 110 may be configured to transmit ultrasound signals in a range that extends from approximately two megahertz (MHz) to approximately 10 or more MHz (e.g., 18 MHz). In other implementations, ultrasound probe 110 may be configured to transmit ultrasound signals in a different range. Furthermore, ultrasound probe 110 may house one or more motors for controlling the movement of the ultrasound transducer(s).

Ultrasound probe 110 may include a handle 112, a trigger 114, and a dome 118 (also referred to as a "nose"). A user (e.g., a medical practitioner, etc.) may hold ultrasound probe 110 via handle 112 and press trigger 114 to activate one or more ultrasound transceivers and transducers located in dome 118 to transmit ultrasound signals toward a patient's area of interest (e.g., a particular body organ, a body joint, a blood vessel, etc.). For example, probe 110 may be positioned on a pelvic area of a patient and over the patient's bladder.

Handle 112 enables a user to move probe 110 relative to a patient's area of interest. Activation of trigger 114 may initiate an ultrasound scan of a selected anatomical portion while dome 118 is in contact with a surface portion of a patient's body when the patient's area of interest is scanned. In some implementations, trigger 114 may include a toggle switch 116. Toggle switch 116 may be used to toggle between different views and/or frames of reference, between different scanning modes, between different imaging modes, etc., during an aiming mode of ultrasound system 100. In other implementations, trigger 114 may not include a separate toggle switch 116 and trigger 114 may be used to toggle between different views and/or frames of reference, scanning modes, and/or imaging modes. In yet other implementations, toggle switch 116 may be located in a different location of ultrasound probe 110, and/or may be located on base unit 120. In yet other implementations, a toggling function may be executed via a touchscreen button on the display of base unit 120 and/or via another type of control, such as a microphone (e.g., via spoken commands).

Dome 118 may enclose one or more ultrasound transducers and may be formed from a material that provides an appropriate acoustical impedance match to the anatomical portion and/or permits ultrasound energy to be properly focused as it is projected into the anatomical portion. Dome 118 may also include transceiver circuitry that includes a transmitter and a receiver to transmit and receive ultrasound signals. Probe 110 may communicate with base unit 120 via a wired connection, such as via cable 130. In other implementations, probe 110 may communicate with base unit 120 via a wireless connection (e.g., Bluetooth, WiFi, etc.).

Base unit 120 may house and include one or more processors or processing logic configured to process reflected ultrasound energy that is received by probe 110 to produce an image of the scanned anatomical region. Furthermore, base unit 120 may include display 122 to enable a user to view images from an ultrasound scan, and/or to enable operational interaction with respect to the user during operation of probe 110. For example, display 122 may include an output display/screen, such as a liquid crystal display (LCD), light emitting diode (LED) based display, touchscreen, and/or another type of display that provides text and/or image data to a user.

For example, display 122 may provide instructions for positioning probe 110 relative to a selected anatomical portion of a patient. Alternatively, ultrasound probe 110 may include a small display (e.g., in handle 112) that provides instructions for positioning ultrasound probe 110. Display 122 may also display two-dimensional or three-dimensional images of the selected anatomical region. In some implementations, display 122 may include a graphical user interface (GUI) that allows the user to select various features associated with an ultrasound scan. For example, display 122 may include selection items (e.g., buttons, dropdown menu items, checkboxes, etc.) to select an aiming mode for probe 110 and/or to initiate a 3D scan after probe 110 has been successfully positioned with respect to the patient's area of interest. Furthermore, display 122 may include selection items to select particular types of ultrasound images to be obtained, such as B-mode images, P-mode images, segmentation map mode images, Doppler ultrasound images, harmonic mode images, M-mode images, and/or other types of ultrasound images. Moreover, display 122 may include selection items to select different views and/or frames of reference, scanning modes, and/or imaging modes. Additionally, display 122 may include a selection item to select whether to toggle manually or automatically between the selected views and/or frames of reference, scanning modes, and/or imaging modes.

Figure 1B:
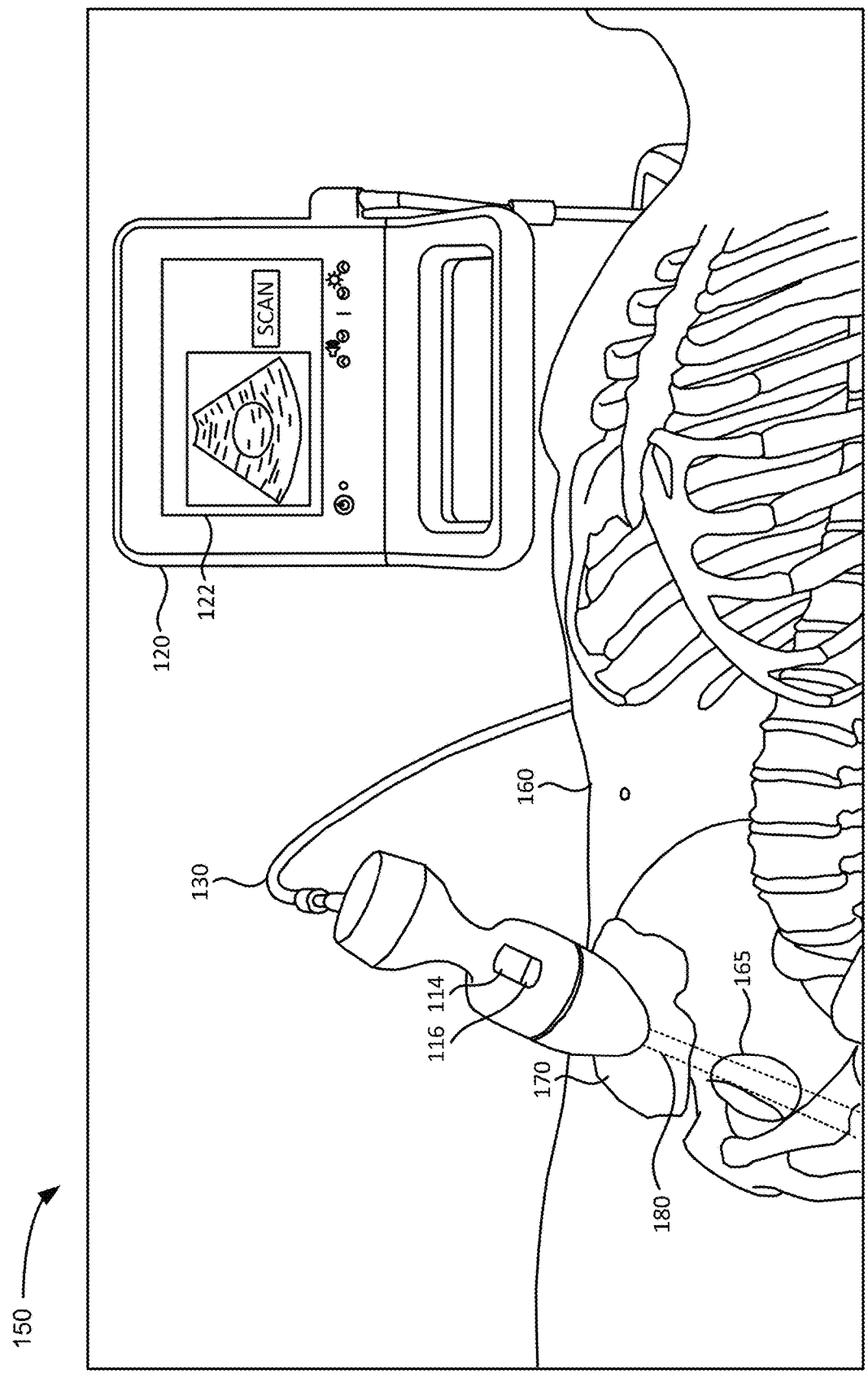
FIG. 1B is a diagram illustrating an exemplary environment for the ultrasound system of FIG. 1A according to an implementation described herein.

FIG. 1B is a diagram illustrating an exemplary environment 150 for ultrasound system 100 according to an implementation described herein. Environment 150 illustrates the operation of ultrasound system 100 with respect to a patient 160. As shown in FIG. 1B, patient 160 may be positioned so that a patient's target of interest may be scanned. For example, assume the target of interest corresponds to the patient's bladder 165. To scan bladder 165, ultrasound probe 110 may be positioned against a surface portion of patient 160 that is proximate to the anatomical portion to be scanned. The user may apply acoustic gel 170 (or gel pads) to the skin of patient 160 over the area of bladder 165 to provide an acoustical impedance match when dome 118 is placed against the skin.

The user may select an aiming mode via base unit 120 (e.g., by selecting an aiming mode button, menu item, etc., on display 122, by speaking a voice command, etc.). Alternatively, an aiming mode may be selected automatically when base unit 120 detects motion of ultrasound probe 110 or ultrasound probe 110 contacts acoustic gel 170 or the skin of patient 160 (e.g., via an accelerometer and/or gyroscope inside ultrasound probe 110). Ultrasound probe 110 may transmit ultrasound signals 180 through bladder 165 and may receive reflected ultrasound signals. The reflected ultrasound signals may be processed into images that are displayed on display 122.

In some implementations, the user may select different views and/or frames of reference, scanning modes, and/or imaging modes. In other implementations, one or more views and/or frames of reference, scanning modes, and/or imaging modes may be selected automatically without user input. In some implementations, display 122 may toggle between the selected views and/or frames of reference, scanning modes, and/or imaging modes automatically, without user input and/or without the user changing the position of ultrasound probe 110. In other implementations, the user may toggle between the selected views and/or frames of reference, scanning modes, and/or imaging modes using toggle switch 116. In yet other implementations, one or more of the selected views and/or frames of reference, scanning modes, and/or imaging modes may be displayed simultaneously on display 122. The user may adjust the position of ultrasound probe 110 based on the information displayed on display 122 until ultrasound probe 110 is centered with respect to bladder 165 and aligned to capture ultrasound images with a maximum cross-section of bladder 165. In some implementations, when ultrasound probe 110 is centered and aligned, a 3D scan may be initiated automatically. In other implementations, the user may activate a 3D scan of bladder 165 by pressing trigger 114, by pressing a scan button on display 122, by speaking a voice command, and/or using another type of scan activation technique.

Although FIGS. 1A and 1B show exemplary components of ultrasound system 100, in other implementations, ultrasound system 100 may include fewer components, different components, additional components, or differently arranged components than depicted in FIGS. 1A and 1B. Additionally or alternatively, one or more components of ultrasound system 100 may perform one or more tasks described as being performed by one or more other components of ultrasound system 100.

For example, in other embodiments, ultrasound probe 110 may correspond to a self-contained device that includes a microprocessor housed within ultrasound probe 110, configured to operably control the one or more ultrasound transducers, and to process the reflected ultrasound energy to generate ultrasound images. Accordingly, a display on ultrasound probe 110 may be used to display the generated images and/or to view other information associated with the operation of ultrasound probe 110. In yet other implementations, ultrasound probe 110 may be coupled to a general-purpose computer, such as a laptop, tablet, and/or a desktop computer (via a wired or wireless connection) that includes software that at least partially controls the operation of ultrasound probe 110 and/or that includes software to process information received from ultrasound probe 110 to generate ultrasound images.

Figure 2A:
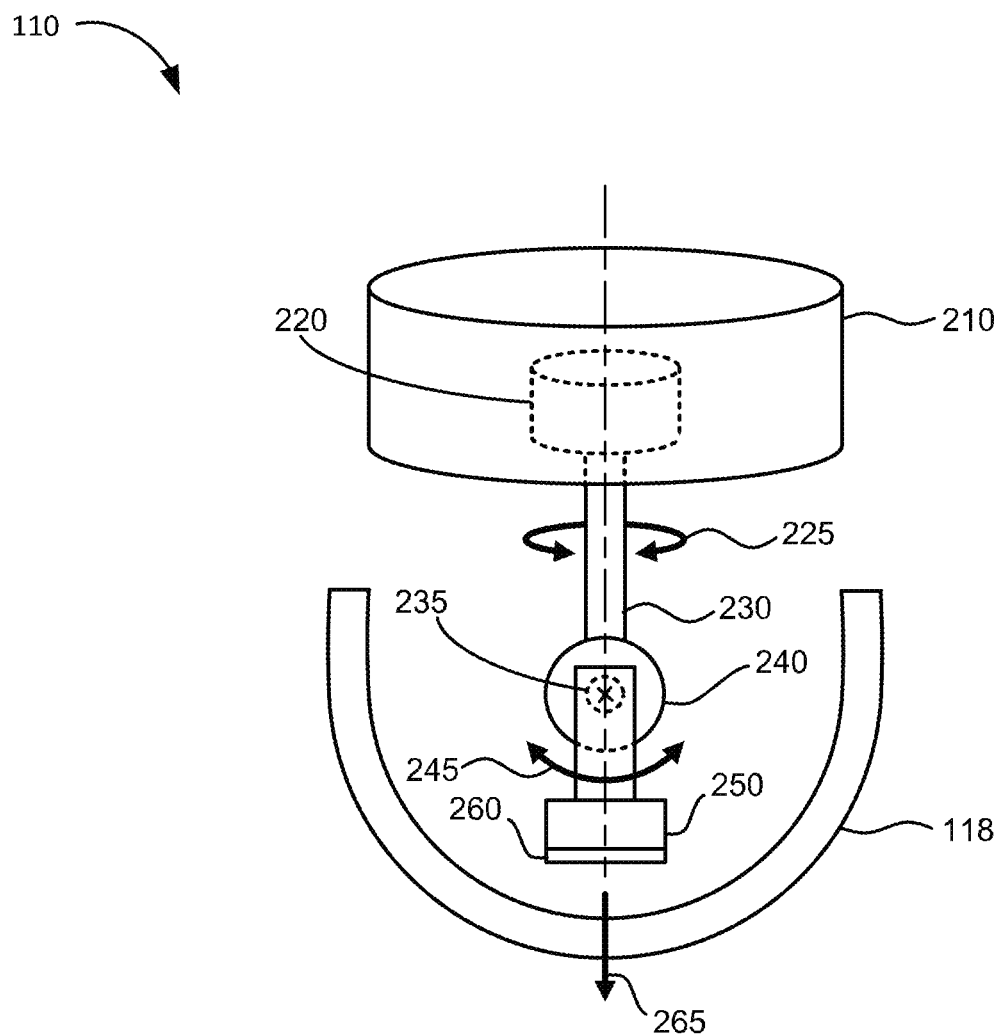
FIG. 2A is a diagram of a first exemplary ultrasound probe according to an implementation described herein.

FIG. 2A is a diagram of a first exemplary implementation of ultrasound probe 110 according to an implementation described herein. As shown in FIG. 2A, ultrasound probe 110 may include a single transducer element coupled to two rotational motors. In this implementation, ultrasound probe 110 may include a base 210 connected to dome 118, a theta motor 220, a spindle 230, a phi motor 240, and a transducer bucket 250 with a transducer 260. Theta motor 220, phi motor 240, and/or transducer 260 may include wired or wireless electrical connections that electrically connect theta motor 220, phi motor 240, and/or transducer 260 to base unit 120 via cable 130 (not shown in FIG. 2A).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in a longitudinal direction with respect to transducer 260, by rotating around a vertical axis referred to herein as a theta ($\theta$) rotational plane 225. Spindle 230 may terminate in a shaft 235 and phi motor 240 may be mounted onto shaft 235. Phi motor 240 may rotate around an axis orthogonal to the theta rotational plane 225 around a horizontal axis referred to herein as a phi ($\phi$) rotational plane 245. Transducer bucket 250 may be mounted to phi motor 240 and may move with phi motor 240.

Transducer 260 may be mounted to transducer bucket 250. Transducer 260 may include a piezoelectric transducer, a capacitive transducer, and/or another type of ultrasound transducer. Transducer 260, along with transceiver circuitry associated with transducer 260, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 260 may transmit and receive ultrasound signals in a signal direction 265 that is substantially perpendicular to the surface of transducer 260.

Signal direction 265 may be controlled by the movement of phi motor 240 and the orientation of phi motor 240 may be controlled by theta motor 220. For example, phi motor 240 may rotate back and forth across an angle that is less than 180 degrees to generate ultrasound image data for a particular plane and theta motor 220 may rotate to particular positions to obtain ultrasound image data for different planes.

In an aiming mode, theta motor 220 may remain stationary while phi motor 240 rotates back and forth to obtain ultrasound image data for a particular aiming plane. In the aiming mode, theta motor 220 may move back and forth between multiple aiming planes and phi motor 240 may rotate back and forth to obtain ultrasound image data. As an example, theta motor 220 may move back between two orthogonal planes while the aiming mode is selected. As another example, theta motor 220 may sequentially rotate through three planes offset by 120 degrees to each other during the aiming mode.

In a 3D scan mode, theta motor 220 may cycle through a set of planes one or more times to obtain a full 3D scan of an area of interest. In each particular plane of the set of planes, phi motor 240 may rotate to obtain B-mode image data for the particular plane. The movement of theta motor 220 and phi motor 240 may be interlaced in the 3D scan motor. For example, the movement of phi motor 240 in a first direction may be followed by a movement of theta motor 220 from a first plane to a second plane, followed by the movement of phi motor 240 in a second direction opposite to the first direction, followed by movement of theta motor 220 from the second plane to a third plane, etc. Such interlaced movement may enable ultrasound probe 110 to obtain smooth continuous volume scanning as well as improving the rate at which the scan data is obtained.

Figure 2B:
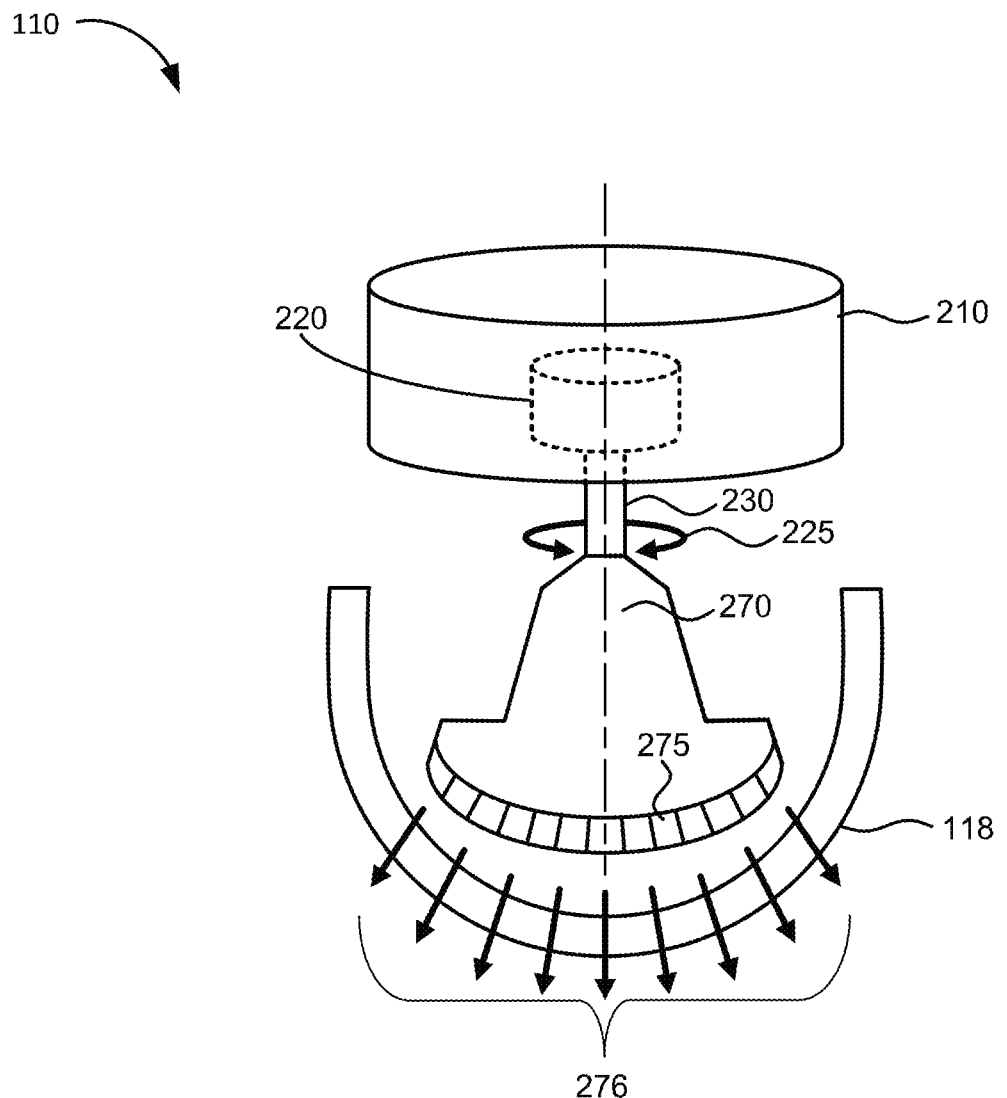
FIG. 2B is a diagram of a second exemplary ultrasound probe according to an implementation described herein.

FIG. 2B is a diagram of a second exemplary implementation of ultrasound probe 110 according to an implementation described herein. As shown in FIG. 2B, ultrasound probe 110 may include a one-dimensional (1D) array of transducer elements coupled to a rotation motor. In this implementation, ultrasound probe 110 may include a base 210 connected to dome 118, a theta motor 220, a spindle 230, and a transducer bucket 270 with a 1D transducer array 275. Theta motor 220 and/or 1D transducer array 275 may include wired or wireless electrical connections that electrically connect theta motor 220 and/or 1D transducer array 275 to base unit 120 via cable 130 (not shown in FIG. 2B).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in longitudinal direction with respect to 1D transducer array 275 by rotating around theta rotational plane 225. Spindle 230 may terminate in transducer bucket 270. 1D transducer array 275 may be mounted to transducer bucket 270. 1D transducer array 275 may include a curved 1D array of piezoelectric transducers, capacitive transducers, and/or other types of ultrasound transducers. 1D transducer array 275 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 1D transducer array 275 may transmit and receive ultrasound signals in a particular direction of a set of directions, illustrated as item 276 in FIG. 2B. Thus, together, the elements of 1D transducer array 275 may generate ultrasound image data for a particular plane.

In an aiming mode, theta motor 220 may remain stationary while 1D transducer array 275 obtains ultrasound image data for a particular aiming plane. In the aiming mode, theta motor 220 may move back and forth between multiple aiming planes and 1D transducer array 275 may obtain ultrasound image data in each aiming plane. As an example, theta motor 220 may move back between two orthogonal planes while aiming mode is selected. As another example, theta motor 220 may sequentially rotate through three planes located 120 degrees apart from each other. In a 3D scan mode, theta motor 220 may cycle through a set of planes one or more times to obtain a full 3D scan of an area of interest. In each particular plane of the set of planes, 1D transducer array 275 may obtain ultrasound image data for the particular plane.

Figure 2C:
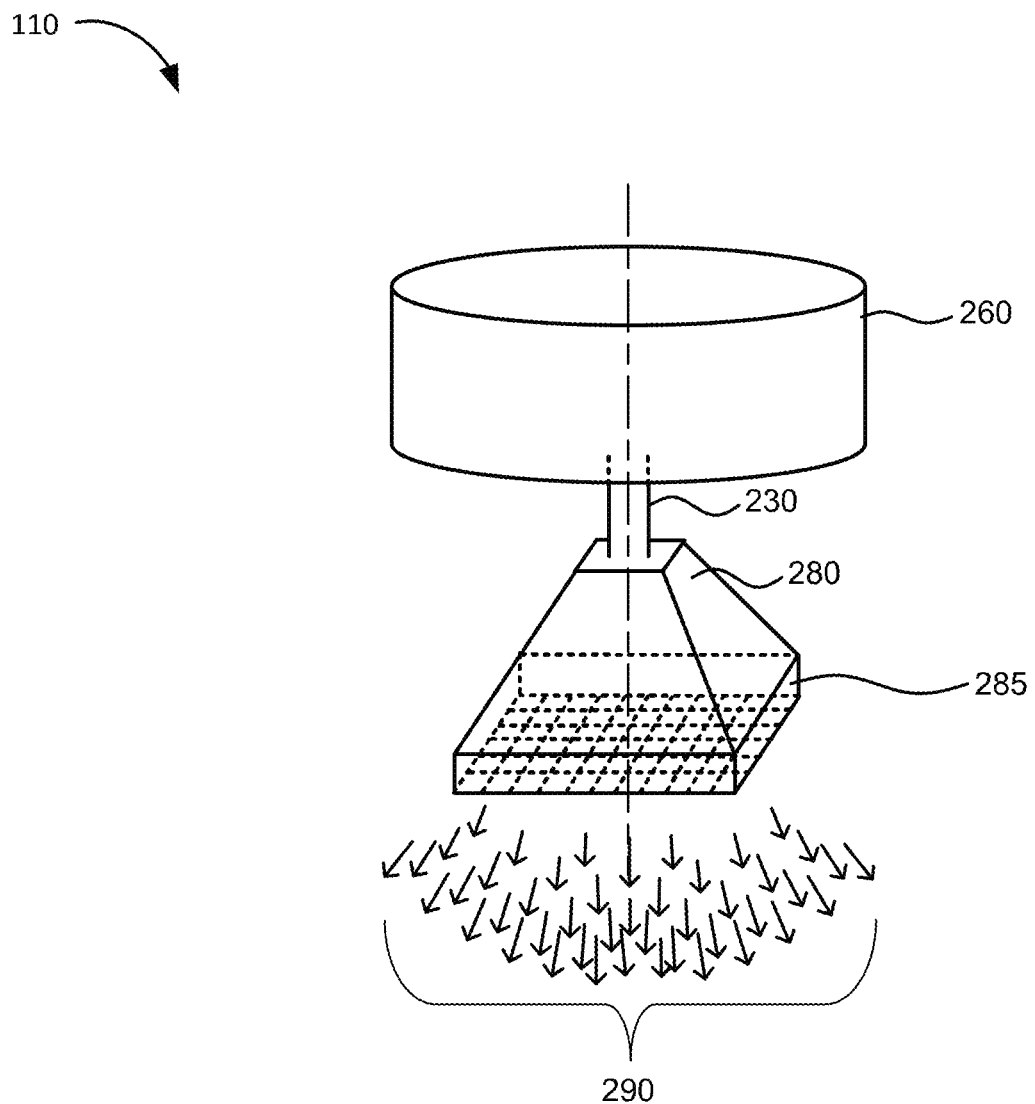
FIG. 2C is a diagram of a third exemplary ultrasound probe according to an implementation described herein.

FIG. 2C is a diagram of a third exemplary ultrasound probe 110 according to an implementation described herein. As shown in FIG. 2C, ultrasound probe 110 may include a two-dimensional (2D) array of transducer elements. In this implementation, ultrasound probe 110 may include a base 210, a spindle 230, and a transducer bucket 280 with a 2D transducer array 285. 2D transducer array 285 may include wired or wireless electrical connections that electrically connects 2D transducer array 285 to base unit 120 via cable 130 (not shown in FIG. 2C).

Base 210 may provide structural support to ultrasound probe 110 and secure spindle 230. Spindle 230 may terminate in transducer bucket 280. 2D transducer array 285 may be mounted to transducer bucket 280. 2D transducer array 285 may include a 2D array of piezoelectric transducers, capacitive transducers, and/or other types of ultrasound transducers. 2D transducer array 285 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 2D transducer array 285 may transmit and receive ultrasound signals in a particular direction of a set of directions, illustrated as item 290 in FIG. 2C. Thus, together, the elements of 2D transducer array 285 may generate ultrasound image data for multiple planes to generate a 3D ultrasound scan. In other words, 2D transducer array 285 may be controlled to tilt an ultrasound beam electronically in a particular direction.

In an aiming mode, 2D transducer array 285 may obtain ultrasound image data for one or more selected aiming planes. For a particular selected aiming plane, a linear 1D set of transducer elements from 2D transducer array 285 may be selected to generate an ultrasound image for the particular selected aiming plane. As an example, two 1D sets of transducers may be selected for two orthogonal planes and may alternate between obtaining ultrasound images of the two orthogonal planes. Alternatively, the ultrasound images for the two orthogonal planes may be obtained substantially simultaneously. As another example, 2D transducer array 285 may cycle through three planes located 120 degrees apart from each other and three sets of 1D sets of transducer elements from 2D transducer array 285 may obtain the ultrasound images for the three planes. In a 3D scan mode, 2D transducer array 285 may cycle through sets of 1D sets of transducer elements one or more times to obtain a full 3D scan of an area of interest. Alternatively, multiple sets of 1D sets of transducer elements, or even all of the transducer elements, of 2D transducer array 285 may be activated substantially simultaneously to obtain a full 3D scan of the area of interest.

Although FIGS. 2A, 2B, and 2C show exemplary components of ultrasound probe 110, in other implementations, ultrasound probe 110 may include fewer components, different components, additional components, or differently arranged components than depicted in FIGS. 2A, 2B, and 2C. Additionally or alternatively, one or more components of ultrasound probe 110 may perform one or more tasks described as being performed by one or more other components of ultrasound probe 110.

Figure 3:
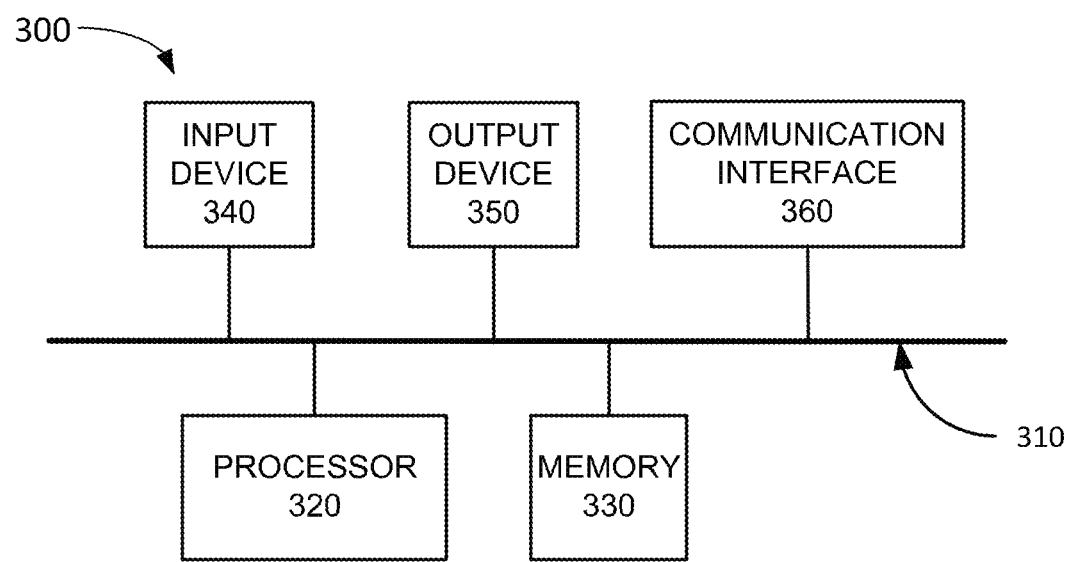
FIG. 3 is a diagram illustrating exemplary components of elements of FIG. 1A.

FIG. 3 is a diagram illustrating example components of a device 300 according to an implementation described herein. Ultrasound probe 110 and/or base unit 120 may each include one or more devices 300. As shown in FIG. 3, device 300 may include a bus 310, a processor 320, a memory 330, an input device 340, an output device 350, and a communication interface 360.

Bus 310 may include a path that permits communication among the components of device 300. Processor 320 may include any type of single-core processor, multi-core processor, microprocessor, latch-based processor, and/or processing logic (or families of processors, microprocessors, and/or processing logics) that interprets and executes instructions. In other embodiments, processor 320 may include an application-specific integrated circuit (ASIC), a field-programmable gate array (FPGA), and/or another type of integrated circuit or processing logic.

Memory 330 may include any type of dynamic storage device that may store information and/or instructions, for execution by processor 320, and/or any type of non-volatile storage device that may store information for use by processor 320. For example, memory 330 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 340 may allow an operator to input information into device 300. Input device 340 may include, for example, a keyboard, a mouse, a pen, a microphone, a remote control, an audio capture device, an image and/or video capture device, a touch-screen display, and/or another type of input device. In some embodiments, device 300 may be managed remotely and may not include input device 340. In other words, device 300 may be "headless" and may not include a keyboard, for example.

Output device 350 may output information to an operator of device 300. Output device 350 may include a display, a printer, a speaker, and/or another type of output device. For example, device 300 may include a display, which may include a liquid-crystal display (LCD), light emitting diode (LED) display, etc., for displaying content to the operator. In some embodiments, device 300 may be managed remotely and may not include output device 350. In other words, device 300 may be "headless" and may not include a display, for example.

Communication interface 360 may include a transceiver that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 360 may include a transmitter that converts baseband signals to radio frequency (RF) signals and/or a receiver that converts RF signals to baseband signals. Communication interface 360 may be coupled to an antenna for transmitting and receiving RF signals.

Communication interface 360 may include a logical component that includes input and/or output ports, input and/or output systems, and/or other input and output components that facilitate the transmission of data to other devices. For example, communication interface 360 may include a network interface card (e.g., Ethernet card) for wired communications and/or a wireless network interface (e.g., a WiFi) card for wireless communications. Communication interface 360 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 300 may perform certain operations relating to symbolic or pictographic representation of a target during an aiming mode. Device 300 may perform these operations in response to processor 320 executing software instructions contained in a computer-readable medium, such as memory 330. A computer-readable medium may be defined as a non-transitory memory device. A memory device may be implemented within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of, or in combination with, software instructions to implement processes described herein. Thus, implementations described herein are not limited to any specific combination of hardware circuitry and software.

Although FIG. 3 shows exemplary components of device 300, in other implementations, device 300 may include fewer components, different components, additional components, or differently arranged components than depicted in FIG. 3. Additionally, or alternatively, one or more components of device 300 may perform one or more tasks described as being performed by one or more other components of device 300.

Figure 4:
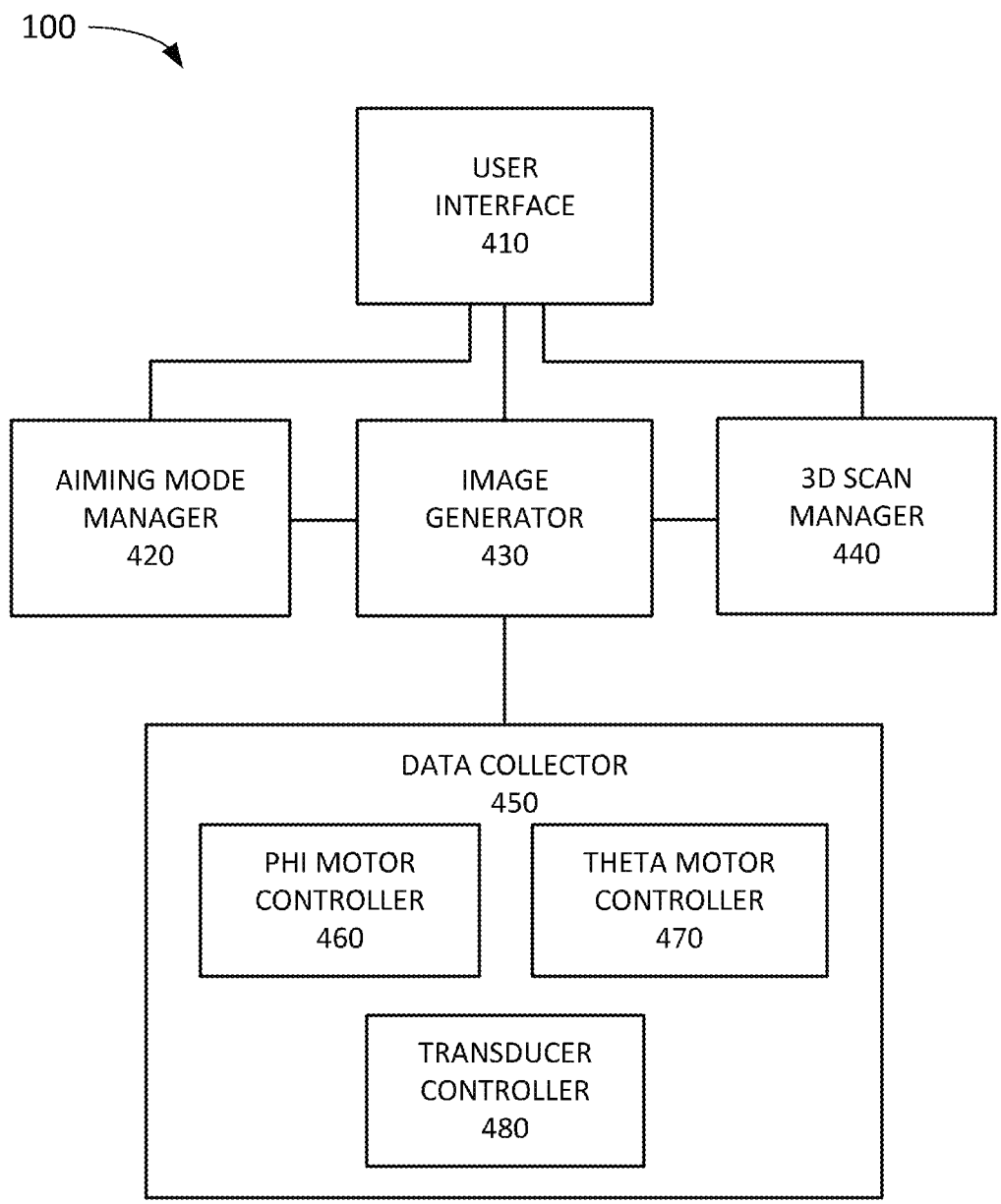
FIG. 4 is a diagram illustrating exemplary functional components of the system of FIG. 1A.

FIG. 4 is a diagram illustrating exemplary functional components of ultrasound system 100. In other implementations, the components of FIG. 4 may be implemented in a device that uses a different type of imaging modality, such as, for example, optical imaging, 3D imaging, thermal and/or IR imaging, x-ray imaging, nuclear resonance imaging, and/or another type of imaging. The functional components of ultrasound system 100 may be implemented, for example, via processor 320 executing instructions from memory 330. Alternatively, some or all of the functional components of ultrasound system 100 may be implemented via hard-wired circuitry. As shown in FIG. 4, ultrasound system 100 may include a user interface 410, an aiming mode manager 420, an image generator 430, a 3D scan manager 440, and a data collector 450.

User interface 410 may generate a user interface (e.g., a graphical user interface) that displays ultrasound images, and/or symbolic or pictographic representations of a target during aiming, to a user via display 122. User interface 410 may be configured to receive selections and/or commands from the user via a touchscreen associated with display 122, via one or more control keys located on base unit 120 and/or on ultrasound probe 110, via a microphone included in base unit 120, and/or via another type of input method. For example, a user may select a type of ultrasound image, an aiming mode via user interface 410, may select different frames of reference, viewing planes, scanning modes, and/or imaging modes, and/or may select to perform a 3D scan once ultrasound probe 110 is centered and aligned during an aiming mode.

Aiming mode manager 420 may manage an aiming mode associated with ultrasound system 100. As an example, when a user selects to perform a scan, ultrasound system 100 may automatically enter an aiming mode. As another example, a user may select an aiming mode using a selection item and/or by executing a particular command. In some implementations, aiming mode manager 420 may select a default frame of reference or viewing plane. Additionally, or alternatively, a user may select one or more frames of reference, viewing planes, scanning modes, and/or imaging modes. As an example, a user may select a first viewing plane by specifying a particular plane (e.g., "sagittal," "transverse," etc.) and/or may select whether to use ultrasound probe 110 as the frame of reference during aiming or whether to use the patient's body as the frame of reference during aiming. As another example, scanning modes may be selected by specifying the number of scanning planes for each selected scanning mode. As yet another example, imaging modes may be selected from a list of available imaging modes.

Aiming mode manager 420 may instruct image generator 430 to obtain/capture ultrasound images using particular types of ultrasound images, such as B-mode ultrasound images, P-mode ultrasound images, Doppler ultrasound images, segmentation map mode ultrasound images, harmonic mode ultrasound images, M-mode ultrasounds images, and/or other types of ultrasound images. Image generator 430 may obtain/capture ultrasound images in particular planes. For example, image generator 430 may instruct data collector 450 to obtain a particular type of ultrasound image, to move to a particular plane (e.g., a particular position of theta motor 220), and to generate an ultrasound image of a particular type for the particular plane (e.g., using phi motor 240 and transducer 260).

Aiming mode manager 420 may generate a symbolic or pictographic representation of a target of interest based on ultrasound images captured by image generator 430 and may display the symbolic or pictographic representation instead of the actual captured ultrasound images when ultrasound system 100 is in an aiming mode. The functionality of aiming mode manager 420 with respect to generating the symbolic or pictographic representation is described in more detail below with reference to FIG. 5.

3D scan manager 440 may generate a 3D scan for an area of interest in a patient's body. For example, in response to ultrasound probe 110 being centered and aligned, and/or in response to a user selecting to perform the 3D scan, 3D scan manager 440 may instruct image generator 430 to generate ultrasound images for a particular set of planes in a particular sequence. In some implementations, the 3D scan may be implemented with an interlaced movement of theta motor 220 and phi motor 240. The number of planes that are scanned during a 3D scan (e.g., the number of different positions of theta motor 220) may be configurable by the user. For example, the 3D scan may be set to scan a plane every 30 degrees, every 15 degrees, every 10 degrees, every 5 degrees, etc.

Data collector 450 may be configured to collect ultrasound image data from ultrasound probe 110. Data collector 450 may include a phi motor controller 460, a theta motor controller 470, and a transducer controller 480. Phi motor controller 460 may control phi motor 240. Theta motor controller 470 may control theta motor 220. Transducer controller 480 may control transducer 260 (or 1D transducer array 275 or 2D transducer array 285).

Although FIG. 4 shows exemplary components of ultrasound system 100, in other implementations, ultrasound system 100 may include fewer components, different components, additional components, or differently arranged components than depicted in FIG. 4. Additionally, or alternatively, one or more components of ultrasound system 100 may perform one or more tasks described as being performed by one or more other components of ultrasound system 100.

Figure 5:
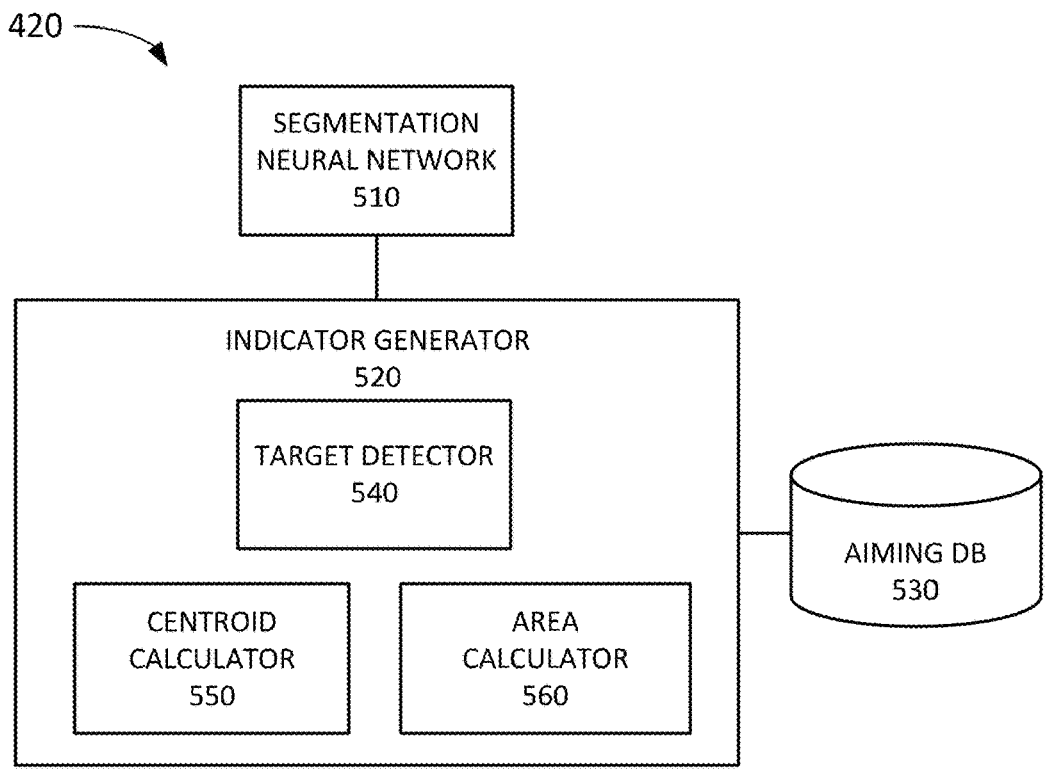
FIG. 5 is a diagram illustrating exemplary functional components of the aiming mode manager of FIG. 4.

FIG. 5 is a diagram illustrating exemplary functional components of aiming mode manager 420. The functional components of aiming mode manager 420 may be implemented, for example, via processor 320 executing instructions from memory 330. Alternatively, some or all of the functional components of aiming mode manager 420 may be implemented via hard-wired circuitry. As shown in FIG. 5, aiming mode manager 420 may include a segmentation neural network 510, an indicator generator 520, and an aiming database (DB) 530.

Segmentation neural network 510 may include a neural network trained to perform segmentation to identify the boundaries of particular types of targets and to generate a boundary around an identified target. For example, segmentation neural network 510 may include one or more convolutional neural networks trained to detect a bladder, a uterus, a prostate, an aorta, or another organ or body structure. Additionally, or alternatively, segmentation neural network 510 may use a different type of segmentation technique, such as, for example, a level-set method, a region growing method, a watershed method, a graph cut method, a dynamic programming method, and/or another type of segmentation technique. In addition to outputting the boundaries of a target, segmentation neural network 510 may be trained to output a confidence level that an ultrasound image includes a particular type of target. For example, segmentation neural network 510 may output a number on the scale of 0 to 1 that represent a percentage likelihood that the ultrasound image includes the particular target (e.g., a bladder).

In some implementations, segmentation neural network 510 may detect clipping of target. Clipping of the target may occur when a part of the target is outside the field of view of ultrasound probe 110. Segmentation neural network 510 may be trained to detect clipping using a set of images that include clipped targets and may detect clipping based on the shape of the detected boundary. If segmentation neural network 510 detects clipping, segmentation neural network 510 may output a clipping flag and aiming mode manager 420 may provide a clipping notification to the user.

Furthermore, in some implementation, segmentation neural network 510 may detect when a target is bigger than the field of view of ultrasound probe 110. Segmentation neural network 510 may be trained to detect targets larger than the field of view using a set of images that include targets being larger than the field of view of an image and may detect such large targets based on the shape of a partially detected boundary, based on other detected structures (e.g., fluid in a bladder), and/or based on textural patterns associated with a particular target. If segmentation neural network 510 detects a target larger than the field of view, segmentation neural network 510 may output a "target larger than field of view" flag and aiming mode manager 420 may provide a "target larger than field of view" notification to the user.

Indicator generator 520 may generate a symbolic or pictographic representation of an identified target based on the boundaries of the target identified by segmentation neural network 510 using information stored in aiming DB 530. Aiming DB 530 may store a set of values used to determine whether ultrasound probe 110 is centered and aligned in order to capture an ultrasound image in which the cross-sectional area of the target of interest is maximized.

Exemplary information that may be stored in aiming DB 530 is described below with reference to FIG. 6.

For example, indicator generator 520 may generate a center indicator and an area indicator for a target of interest based on the identified boundaries of the target. Indicator generator 520 may include a target detector 540, a centroid calculator 550, and an area calculator 560.

Target detector 540 may determine whether a target has been identified by segmentation neural network 510 based on information received from segmentation neural network 510. For example, target detector 540 may determine whether segmentation neural network 510 had identified boundaries for the target and/or whether segmentation neural network 510 has indicated that the likelihood of a captured ultrasound image including the target is above a particular threshold. Indicator generator 520 may not generate a symbolic or pictographic representation of the target until a target has been detected.

Centroid calculator 550 may calculate the centroid of the detected target. The boundaries of the target may be represented as a polygon made of sequential vertices, with the last vertex adjacent to the first vertex. Each vertex may be described by Cartesian x and y coordinates. The area of a non-self-intersecting closed polygon may be computed by the following equation:

$$A = \tfrac{1}{2} \Sigma_{i=0}^{n-1}(x_i y_{i+1} - x_{i+1} y_i) \qquad \text{Eq. (1),}$$

where n is the number of vertices and i is the summation index. The x and y coordinates of the centroid may then be computed as:

$$C_x = \frac{1}{6A} \sum_{i=0}^{n-1} (x_i + x_{i+1})(x_i y_{i+1} - x_{i+1} y_i), \qquad \text{Eq. (2)}$$

$$C_y = \frac{1}{6A} \sum_{i=0}^{n-1} (y_i + y_{i+1})(x_i y_{i+1} - x_{i+1} y_i), \qquad \text{Eq. (3)}$$

where A is the computed area, n is the number of vertices, and i is the summation index. In some implementations, the centroid may be computed using equations (2) and (3). In other implementations, the centroid may be computed as the center between a left-most vertex and a right-most vertex of the vertices of the polygon of the boundary of the target, in order to take into account targets with unusual shapes. Area calculator 560 may calculate a current area of the detected target based on equation (1) and/or based on another technique for computing the area within the identified boundaries of the target.

Indicator generator 520 may generate and display the center indicator as a filled circle with a diameter of a particular number of pixels (e.g., 20 pixels, etc.) based on the computed location of the centroid. Indicator generator 520 may keep track of the position of the centroid with respect to the position of the centerline of the field of view of ultrasound probe 110. When the position of the centroid is within a particular number of pixels or distance of the centerline, indicator generator 520 may highlight the center indicator. The center indicator may be generated in a first color, pattern, shading, and/or shape and, when the center indicator is highlighted, the center indicator may be displayed in a second color, pattern, shading, and/or shape.

Indicator generator 520 may generate and display the area indicator as a filled circle with a diameter of a particular number of pixels and centered on the center indicator. In some implementations, the radius of the circle of the area indicator may be based on an area of the target based on the following equation:

$$r = \sqrt{\frac{|A|}{\pi}}, \qquad \text{Eq. (4)}$$

where r is the radius and A is the area computed for the polygon of the boundaries of the target. In other implementations, the radius of the circle for the area may be based on a set value and may not be based on the size of the identified target. When the current area for the identified target has increased and decreased a particular number of times (e.g., three times, etc.) with respect to a particular value, the particular value may be selected as the maximum area. When the current area is within a particular range of the maximum area, after the maximum area has been selected, indicator generator 520 may highlight the area indicator. The area indicator may be generated in a first color, pattern, shading, and/or shape and, when the area indicator is highlighted, the area indicator may be displayed in a second color, pattern, shading, and/or shape. In some implementations, indicator generator 520 may provide a first type of audible and/or haptic feedback when the center indicator is highlighted and provide a second type of audible and/or haptic feedback when the area indicator is highlighted.

After the center indicator and area indicator have been highlighted, aiming mode manager 420 may determine whether ultrasound probe 110 has remained centered and positioned pointing at the maximum area for at least a particular time period. If the ultrasound probe 110 has remained centered and positioned for at least the particular time period, aiming mode manager 420 may exit the aiming mode and instruct 3D scan manager 440 to initiate a 3D scan.

Although FIG. 5 shows exemplary components of aiming mode manager 420, in other implementations, aiming mode manager 420 may include fewer components, different components, additional components, or differently arranged components than depicted in FIG. 5. Additionally, or alternatively, one or more components of aiming mode manager 420 may perform one or more tasks described as being performed by one or more other components of aiming mode manager 420.

Figure 6:
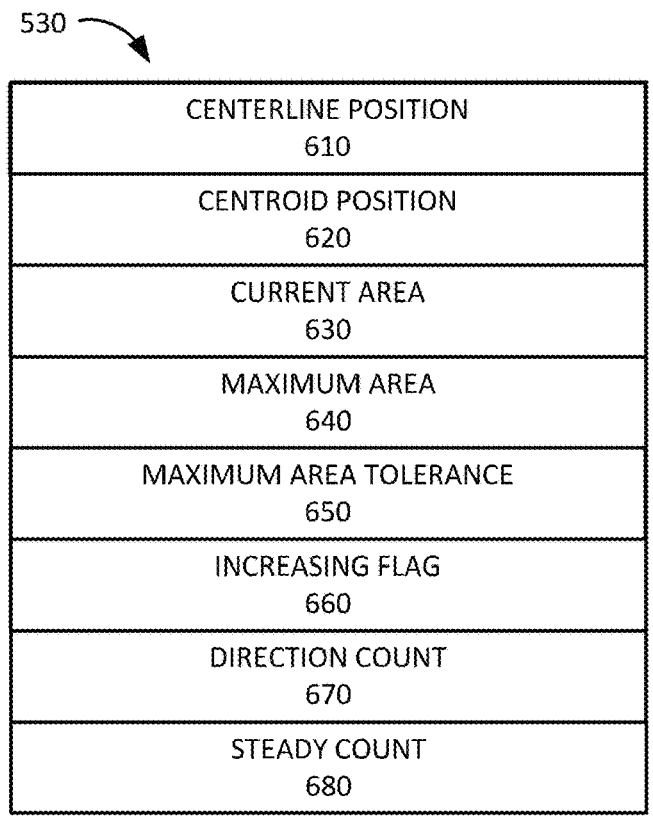
FIG. 6 is a diagram illustrating exemplary components of the aiming database of FIG. 5.

FIG. 6 is a diagram illustrating exemplary components of aiming DB 530. As shown in FIG. 6, aiming DB 530 may include a centerline position entry 610, a centroid position entry 620, a current area entry 630, a maximum area entry 640, a maximum area tolerance entry 650, an increasing flag entry 660, a direction count entry 670, and a steady count entry 680.

Centerline position entry 610 may store information identifying the centerline position of the field of view of ultrasound probe 110. For example, the centerline position may be designated as the centerline of a captured ultrasound image (e.g., a B-mode ultrasound image). Centroid position entry 620 may store information identifying the current or most recently computed centroid position determined by centroid calculator 550.

Current area entry 630 may store information identifying the current or more recently computed area for the target. Maximum area entry 640 may store information identifying the maximum area for the target. Maximum area tolerance entry 650 may store information identifying the maximum area tolerance. The maximum area tolerance may be used to determine how much the current area is allowed to deviate from the maximum area in order to keep the area indicator highlighted.

Increasing flag entry 660 may be used to keep track of whether the current area is increasing. Direction count entry 670 may be used to keep track of the number of times the current area has switched directions from increasing to decreasing and vice versa. The number of times the current area has increased and decreased may be used to determine how many times ultrasound probe 110 has passed through the position associated with the maximum area to ensure the true maximum area has been identified. Steady count entry 680 may be used to keep track of a duration of time that the user has held ultrasound probe 110 in a centered and aligned position. A 3D scan may not be initiated until ultrasound probe 110 has been in a centered and aligned position for at least a particular length of time (e.g., for at least two seconds, etc.).

Figure 7:
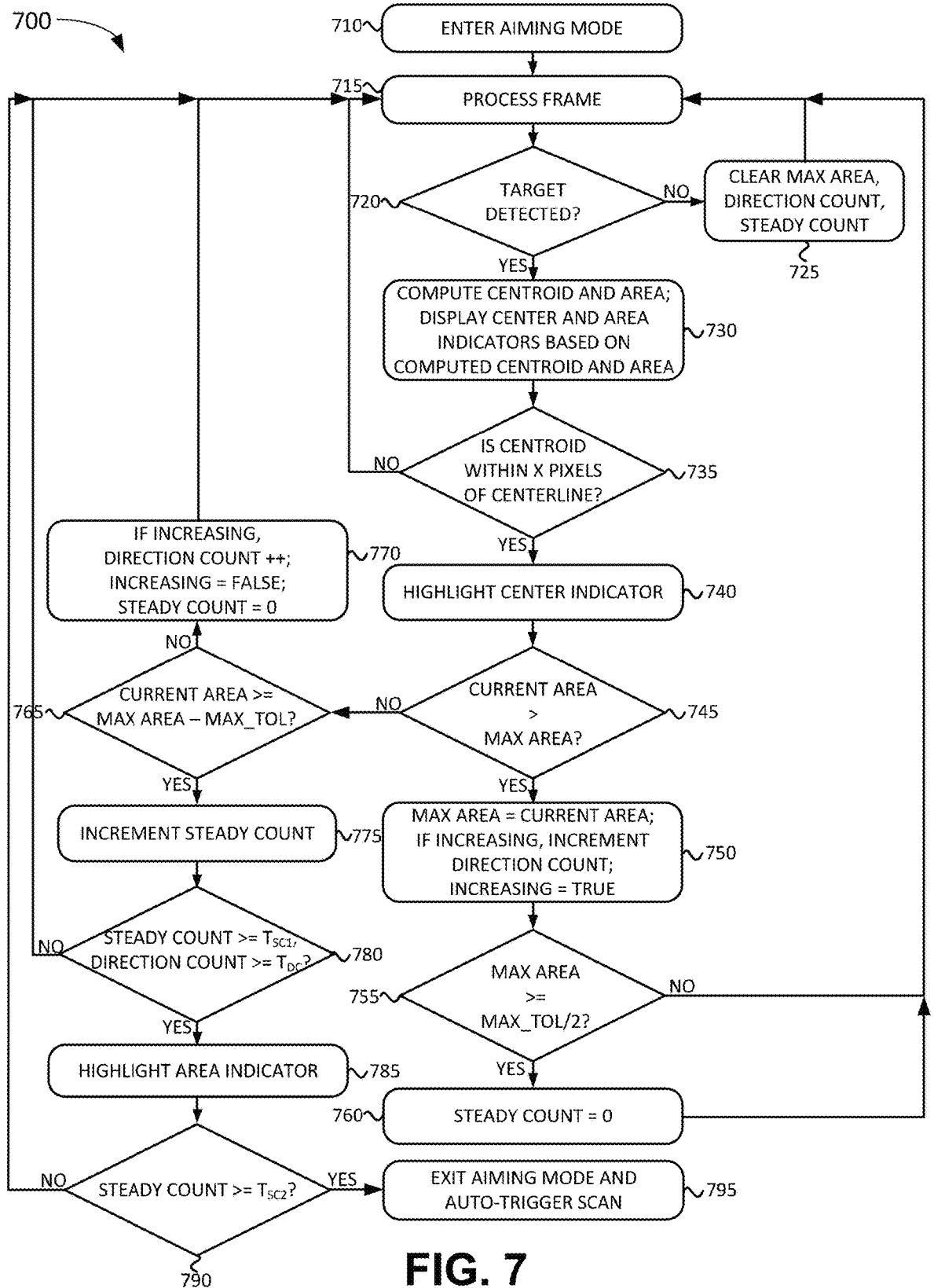
FIG. 7 is a flowchart of a process for generating a user interface during aiming according to an implementation described herein.

FIG. 7 is a flowchart of a process for generating a user interface during aiming according to an implementation described herein. In some implementations, the process of FIG. 7 may be performed by ultrasound system 100. In other implementations, some or all of the process of FIG. 7 may be performed by another device or a group of devices separate from ultrasound system 100. For example, in other implementations, the process of FIG. 7 may be performed by a device that uses a different type of imaging modality, such as, for example, optical imaging, 3D imaging, thermal and/or IR imaging, x-ray imaging, nuclear resonance imaging, and/or another type of imaging.

The process of FIG. 7 may include entering an aiming mode (block 710). As an example, when a user selects to perform a scan and/or turns on ultrasound system 100, ultrasound system 100 may automatically enter an aiming mode. As another example, a user may select an aiming mode using a selection item (e.g., via user interface 410) and/or by executing a particular command. Furthermore, a user may select a particular type of ultrasound image to use during the aiming mode. For example, the user may select to use B-mode ultrasound images, P-mode ultrasound images, Doppler ultrasound images, harmonic mode ultrasound images, M-mode ultrasound images, and/or other types of ultrasound images.

An ultrasound frame may be obtained and processed (block 715) and a determination may be made as to whether the target has been detected in the ultrasound frame (block 720). For example, image generator 430 may capture an ultrasound image via data collector 450 and provide the generated ultrasound image to segmentation neural network 510. Segmentation neural network 510 may perform segmentation to identify the boundaries of a target of interest in the captured ultrasound image and/or output a score that represents the likelihood that the captured ultrasound image includes the target of interest. Target detector 540 may make a determination as to whether the target has been detected in the ultrasound frame based on the output of segmentation neural network 510.

If it is determined that the target was not detected (block 720—NO), maximum area entry 640, direction count entry 670, and steady count entry 680 in aiming DB 530 may be cleared (block 725) and processing may return to block 715 to obtain and process another ultrasound frame. If it is determined that the target was detected (block 720—YES), the centroid and the area of the target may be computed and center and area indicators may be displayed based on the computed centroid and area of the target (block 730).

As an example, centroid calculator 550 may calculate the centroid using equations (2) and (3) and the area using equation (1) above. As another example, centroid calculator 550 may calculate the centroid as the center point between a left-most vertex and a right-most vertex of a polygon defining the boundary of the detected target. Indicator generator 520 may display a center indicator at the position of the computed centroid and an area indicator as a circle, or another type of shape, centered on the center indicator. In some implementations, the size of the area indicator may be based on the computed area using equation (4) above. In other implementations, the size of the area indicator may not be based on the computed area and may be instead based on a default size for the area indicator.

A determination may be made as to whether the centroid is within x number of pixels or distance of the centerline (block 735). For example, indicator generator 520 may compare the computed centroid position with the centerline of the field of view of ultrasound 110 (e.g., the centerline of the ultrasound frame) to determine whether the computed centroid position is within a threshold number of pixels (e.g., ten pixels, etc.) or distance of the centerline. If it is determined that the centroid is not within the x number of pixels or distance of the centerline (block 735—NO), processing my return to block 715 to obtain and process another ultrasound frame. If it is determined that the centroid is within the x number of pixels or distance of the centerline (block 735—YES), the center indicator may be highlighted (block 740). Indicator generator 520 may change the center indicator from a first color, pattern, shading, and/or shape to a second color, pattern, shading, and/or shape. For example, the center indicator may change from a filled red-colored circle to a filled green-colored circle. The user may then be instructed to tilt ultrasound probe 110 in a particular direction (e.g., in a cranial-caudal direction) to identify the maximum cross-sectional area for the target. Additionally, indicator generator 520 may provide audible and/or haptic feedback to the user when the center indicator is highlighted.

A determination may be made as to whether the current area is greater than the maximum area (block 745). For example, indicator generator 520 may compare the value stored in current area entry 630 with maximum area entry 640 to determine whether the current area is greater than the maximum area. The maximum area may be initially set to zero when ultrasound system 100 first enters the aiming mode.

If it is determined that the current area is greater than the maximum area (block 745—YES), the maximum area may be set to the current area; if the increasing flag is set, the direction count may be incremented; and the increasing flag may be set (block 750). For example, indicator generator 520 may store the value from current area entry 630 in maximum area entry 640. Furthermore, if increasing flag entry 660 is set to TRUE, the value in direction count entry 670 may be incremented and increasing flag entry 660 may be set to TRUE. The increasing flag entry 660 may be initially set to FALSE and the direction count entry 670 may be set to zero when ultrasound system 100 first enters the aiming mode.

A determination may be made as to whether the maximum area is greater than or equal to the maximum area tolerance divided by two (block 755). If it is determined that the maximum area is not greater than or equal to the maximum area tolerance divided by two (block 755—NO), processing my return to block 715 to obtain and process another ultrasound frame. If it is determined that the maximum area is greater than or equal to the maximum area tolerance (MAX_TOL) divided by two (block 755—YES), steady count may be set to zero (block 760), and processing my return to block 715 to obtain and process another ultrasound frame.

Returning to block 745, if it is determined that the current area is not greater than the maximum area (block 745—NO), a determination may be made as to whether the current area is greater than or equal to the maximum area minus the maximum area tolerance (block 765). If it is determined that the current area is not greater than or equal to the maximum area minus the maximum area tolerance (block 765—NO), if the increasing flag is set to TRUE, the direction count may be incremented; the increasing flag may be set to FALSE; and the steady count may be set to zero (block 770). Processing may then return to block 715 to obtain and process another ultrasound frame.

If it is determined that the current area is greater than or equal to the maximum area minus the maximum area tolerance (block 765—YES), steady count may be incremented (block 775). A determination may be made as to whether the steady count is greater than or equal to a first steady count threshold $T_{SC1}$ and whether the direction count is greater than or equal to a direction count threshold $T_{DC}$ (block 780). For example, indicator generator 520 may check the values stored in direction count entry 670 and steady count 680 and compare the stored values to predetermined stored thresholds. The direction count threshold $T_{DC}$ may be used to ensure ultrasound probe 110 passed through the maximum area a particular number of times (e.g., three times, five times, etc.) in order to identify the best maximum cross-sectional area of the target. The first steady count threshold $T_{SC1}$ (e.g., five consecutively captured ultrasound frames, etc.) may be used to ensure ultrasound probe 110 has maintained the position of pointing at the maximum cross-sectional area for at least a particular duration.

If it is determined that steady count is not greater than or equal to the first steady count threshold or that the direction count is not greater than or equal to the direction count threshold (block 780—NO), processing may return to block 715 to obtain and process another ultrasound frame. If it is determined that steady count is greater than or equal to the first steady count threshold and that the direction count is greater than or equal to the direction count threshold (block 780—YES), the area indicator may be highlighted (block 785). Indicator generator 520 may change the area indicator from a first color, pattern, shading, and/or shape to a second color, pattern, shading, and/or shape. For example, the area indicator may change from a red circle to a green circle. Additionally, indicator generator 520 may provide audible and/or haptic feedback to the user when the area indicator is highlighted.

A determination may be made as to whether steady count is greater than or equal to a second steady count threshold $T_{SC2}$ (block 790). The second steady count threshold $T_{SC2}$ (e.g., ten consecutively captured ultrasound frames, etc.) may be used to ensure ultrasound probe 110 has maintained the position of pointing at the maximum cross-sectional area for at least a particular duration before a 3D scan is initiated. If it is determined that steady count is not greater than or equal to the second steady count threshold $T_{SC2}$ (block 790—NO), processing may return to block 715 to obtain and process another ultrasound frame. If it is determined that steady count is greater than or equal to the second steady count threshold $T_{SC2}$ (block 790—YES), the aiming mode may be exited and a scan may be auto-triggered (block 795). For example, aiming mode manager 420 may exit aiming mode and instruct 3D scan manager 440 to perform a full 3D scan of the target.

Figure 8A:
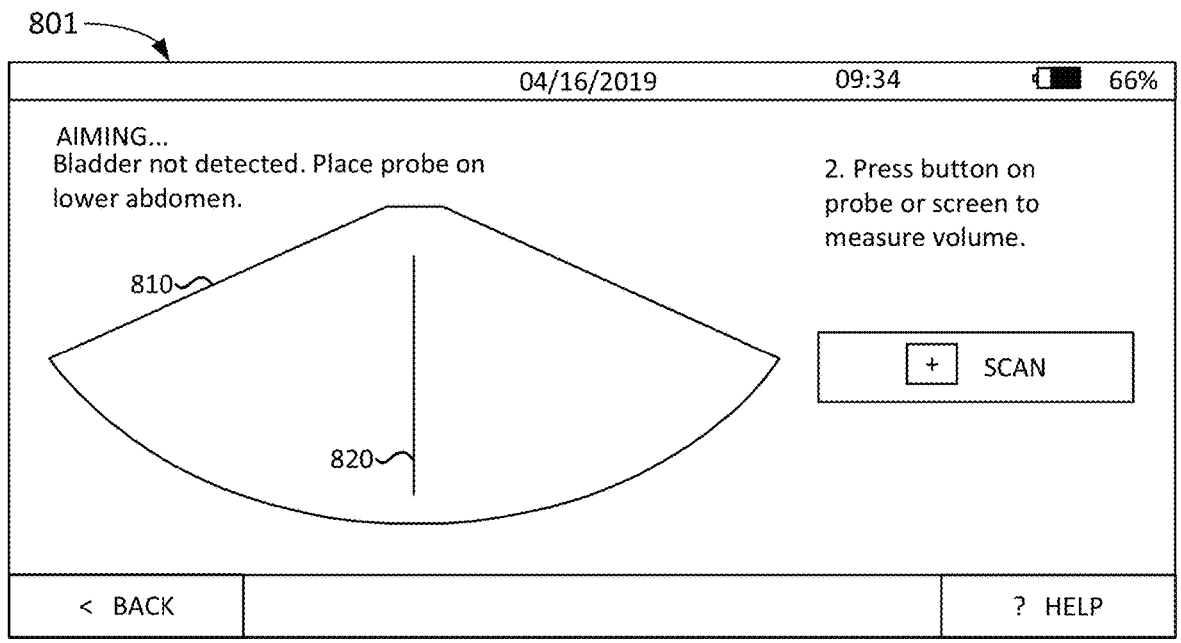
FIGS. 8A-8D are diagrams of user interfaces according to a first implementation described herein.

FIGS. 8A-8D are diagrams of user interfaces that illustrate a B-mode view that uses ultrasound probe 110 as the frame of reference, in which the center indicator and area indicators are moved when the position of ultrasound probe 100 changes. FIG. 8A illustrated a user interface 801 that may be displayed to the user when ultrasound system 100 first enters the aiming mode. User interface 801 may include a field of view 810 and a centerline 820 representing the field of view of ultrasound probe 110 when ultrasound probe 110 captures a B-mode ultrasound image.

Figure 8B:
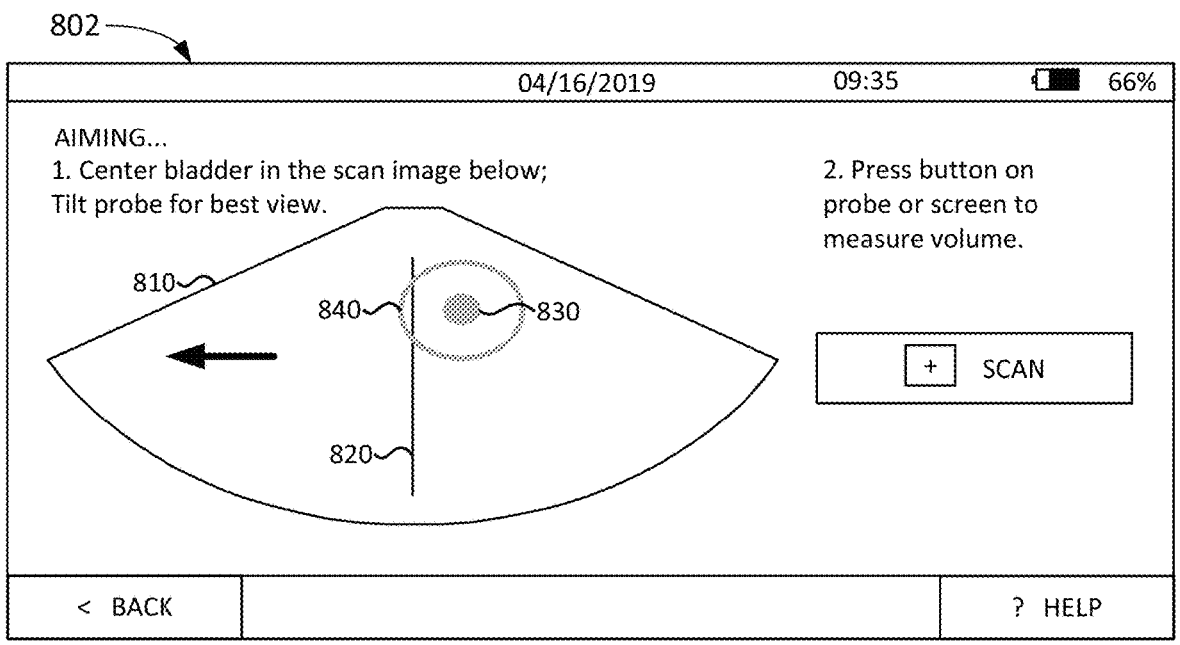
Figure 8C:
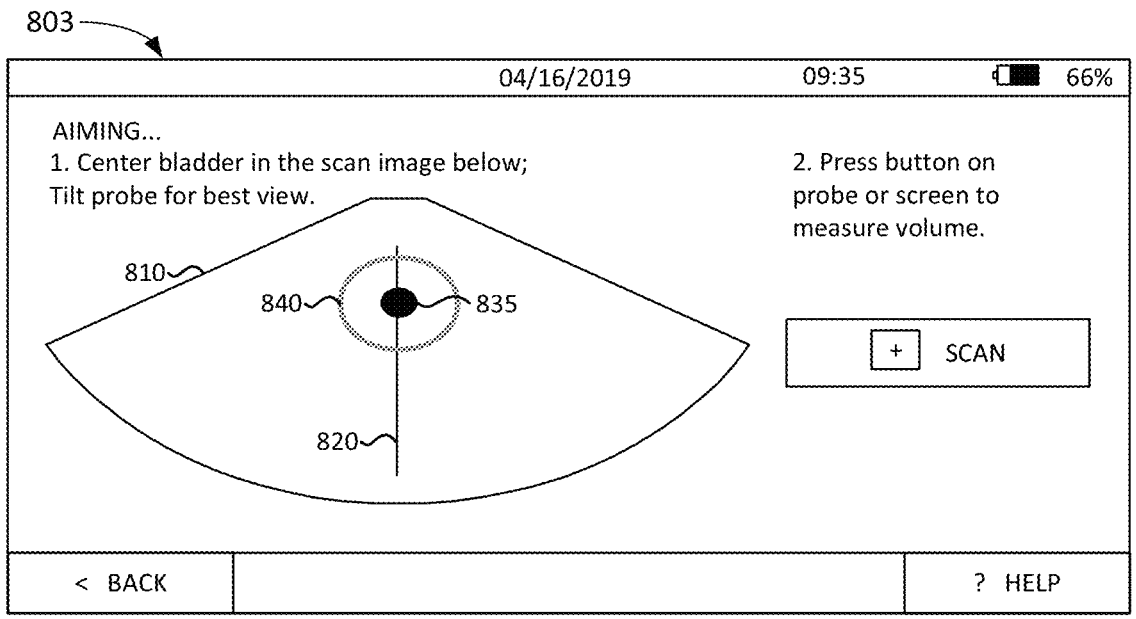

FIG. 8B illustrates user interface 802 after a target is detected. In this example, the target is a patient's bladder. User interface 802 may include a center indicator 830, displayed as, for example, a small filled red-colored circle, and an area indicator 840, displayed as a larger red circle centered on center indicator 830. Center indicator 830 and area indicator 840 represent the position of the bladder in the ultrasound image of field of view 810. FIG. 8C illustrates user interface 803 after ultrasound probe 110 has been centered. When the centroid of the detected bladder is determined to be within a particular number of pixels or distance of centerline 820 (e.g., within ten pixels, etc.), center indicator 830 may be changed to highlighted center indicator 835, corresponding to, for example, a small filled green-colored circle. During centering, the position of center indicator 830 may change as ultrasound probe 110 is moved by the user to reflect the position of center indicator 830 with respect to the bladder. The user may then be instructed to tilt ultrasound probe 110 in a particular direction (e.g., in a cranial-caudal direction) to identify the maximum cross-sectional area for the target.

Figure 8D:
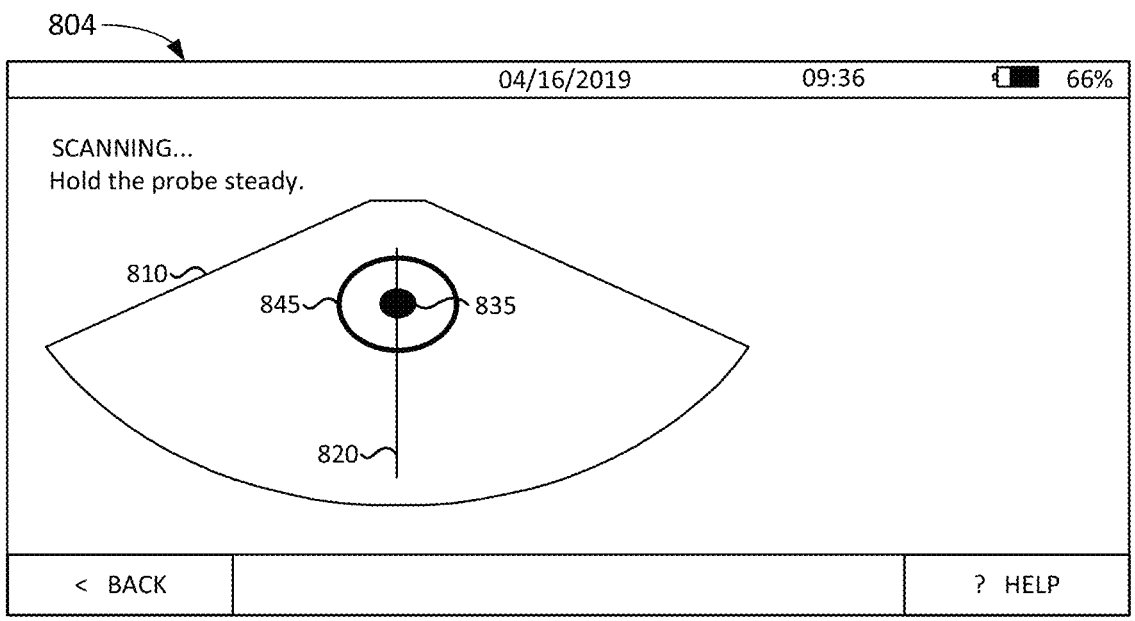

FIG. 8D illustrates user interface 804 after the maximum cross-sectional area of the bladder has been identified and ultrasound probe 110 has been aligned to point at the maximum cross-sectional area. When ultrasound probe 110 is aligned to point at the maximum cross-sectional area of the bladder, area indicator 840 may be changed to highlighted area indicator 845, corresponding to a green circle. After ultrasound probe 110 has been held steady while being centered and pointing at the maximum cross-sectional area for a number of consecutive frame captures, such as ten frames (e.g., corresponding to a time of approximately two seconds), ultrasound system 100 may initiate the 3D scan of the bladder.

Figure 9A:
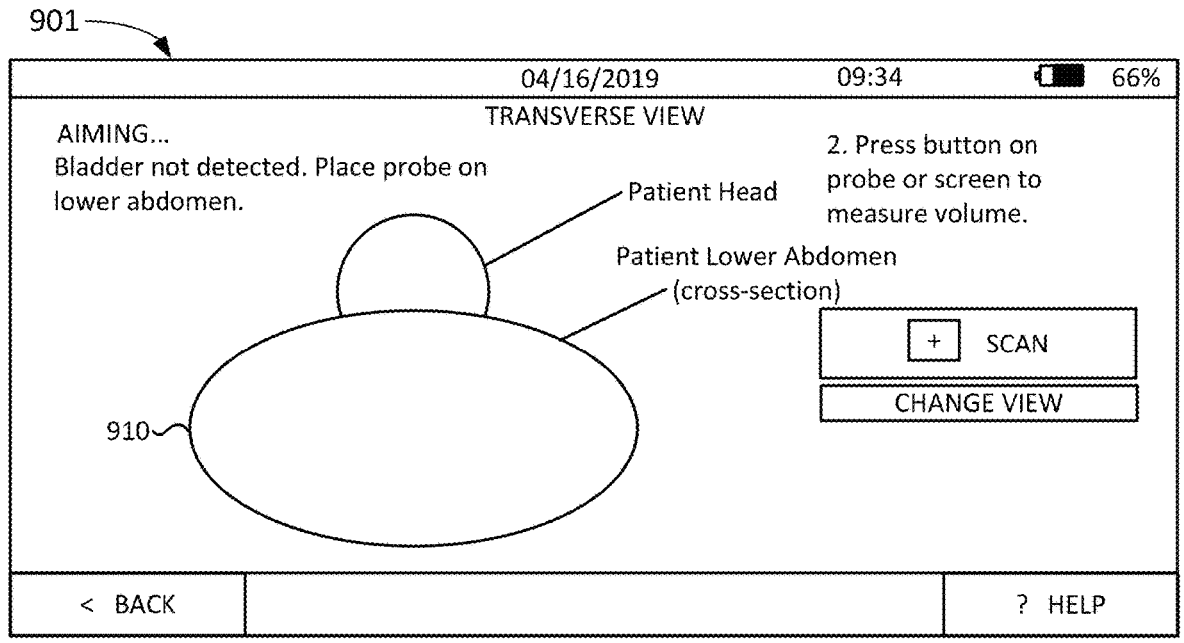
FIGS. 9A-9D are diagrams of user interfaces according to a second implementation described herein.

FIGS. 9A-9D are diagrams of user interfaces that illustrate a transverse view of the patient's body and use the patient's body as the frame of reference. Thus, the patient's body is depicted as being stationary and the field of view of ultrasound probe 110 is moved in the display when ultrasound probe 110 moves. FIG. 9A illustrated a user interface 901 that may be displayed to the user when ultrasound system 100 first enters the aiming mode. User interface 901 may include a transverse plane view 910 of the patient's body.

Figure 9B:
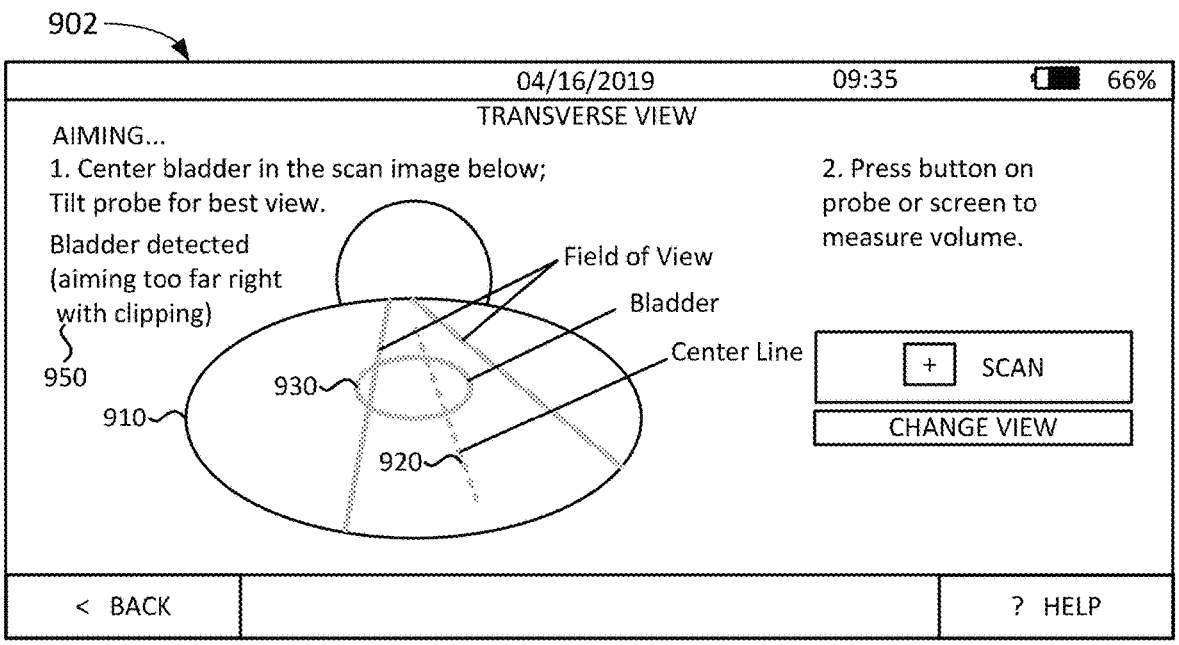

FIG. 9B illustrates user interface 902 after the bladder is detected. User interface 902 may include a field of view of ultrasound probe 110 with a center indicator 920, displayed as the centerline of the field of view. Center indicator 920 may initially be displayed in a red color. Furthermore, user interface 902 may include an area indicator 930, showing the patient's bladder as a red colored oval. If segmentation neural network 510 detects clipping, segmentation neural network 510 may output a clipping flag and aiming mode manager 420 may provide a clipping notification 950 to the user. If segmentation neural network 510 detects a target larger than the field of view, the user may be provided with a "target larger than the field of view" notification and/or may be instructed to reduce pressure on ultrasound probe 110 or add more acoustic gel 170.

Figure 9C:
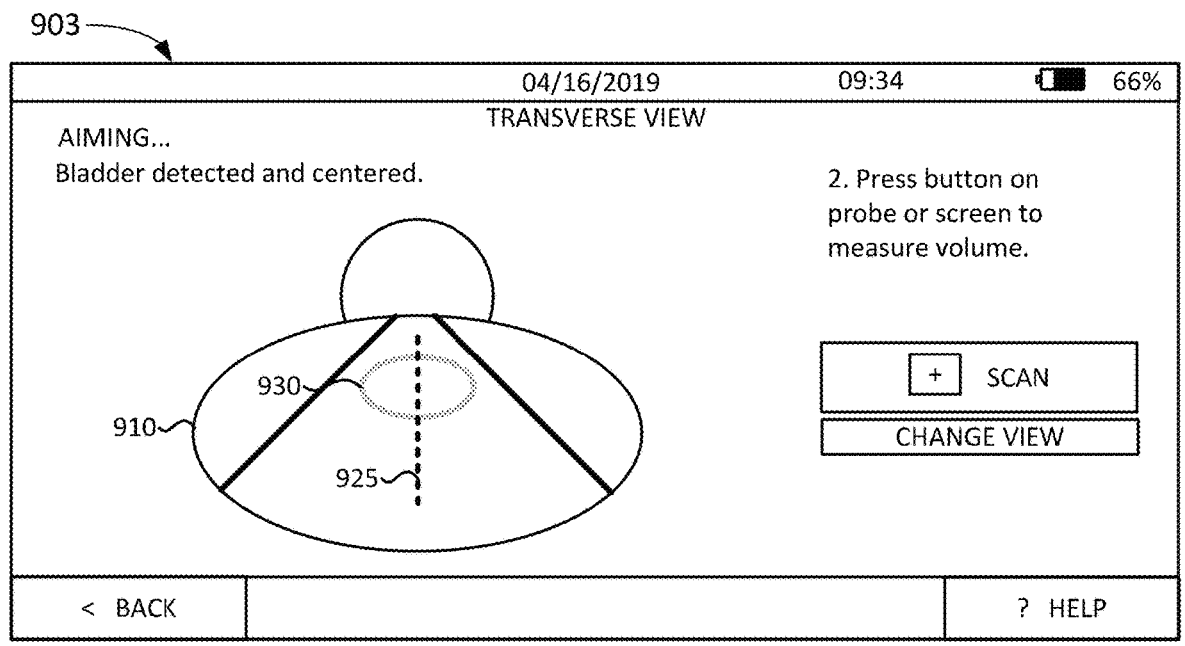

FIG. 9C illustrates user interface 903 after ultrasound probe 110 has been centered. When the centroid of the detected bladder is determined to be within a particular number of pixels or distance of the centerline (e.g., within ten pixels, etc.), center indicator 920 may be changed to highlighted center indicator 925, such as by changing color from red to green. Furthermore, the field of view and highlighted center indicator 925 may be shown as centered on the bladder, represented as area indicator 930. During centering, the position of center indicator 930 may change as ultrasound probe 110 is moved by the user to reflect the position of center indicator 930 with respect to the bladder. The user may then be instructed to tilt ultrasound probe 110 in a particular direction (e.g., in a cranial-caudal direction) to identify the maximum cross-sectional area for the target.

Figure 9D:
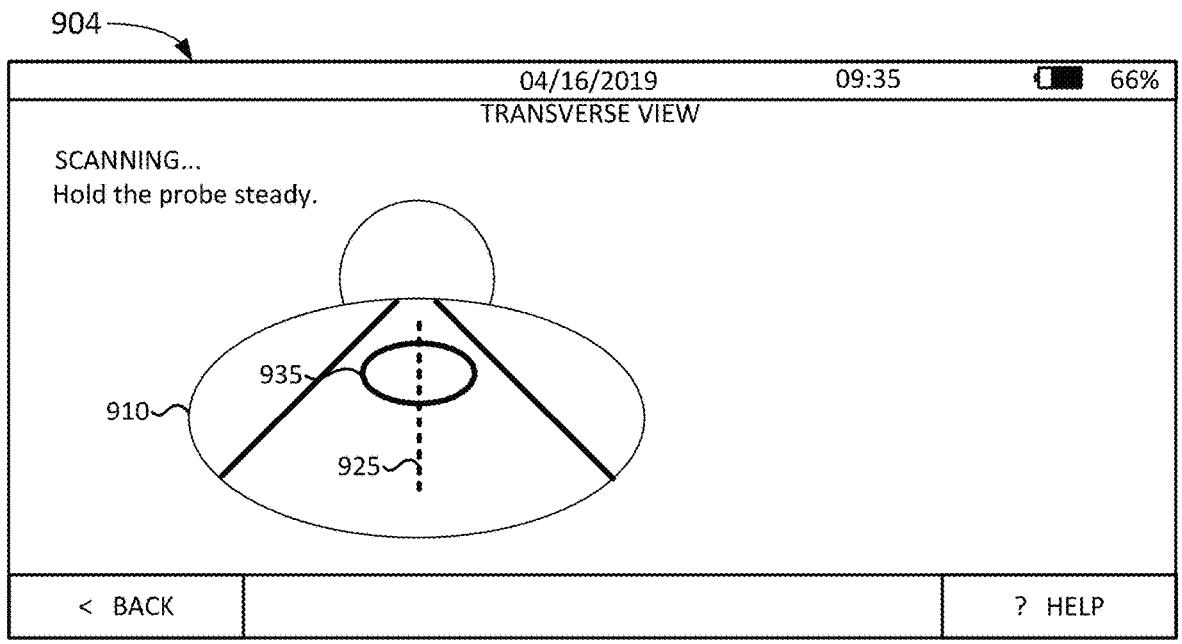

FIG. 9D illustrates user interface 904 after the maximum cross-sectional area of the bladder has been identified and ultrasound probe 110 has been aligned to point at the maximum cross-sectional area. When ultrasound probe 110 is aligned to point at the maximum cross-sectional area of the bladder, area indicator 930 may be changed to highlighted area indicator 935. For example, the color of the oval representing the bladder may change from red to green. After ultrasound probe 110 has been held steady while being centered and pointing at the maximum cross-sectional area for a number of consecutive frame captures, such as ten frames (e.g., corresponding to a time of approximately two seconds), ultrasound system 100 may initiate the 3D scan of the bladder.

Figure 10A:
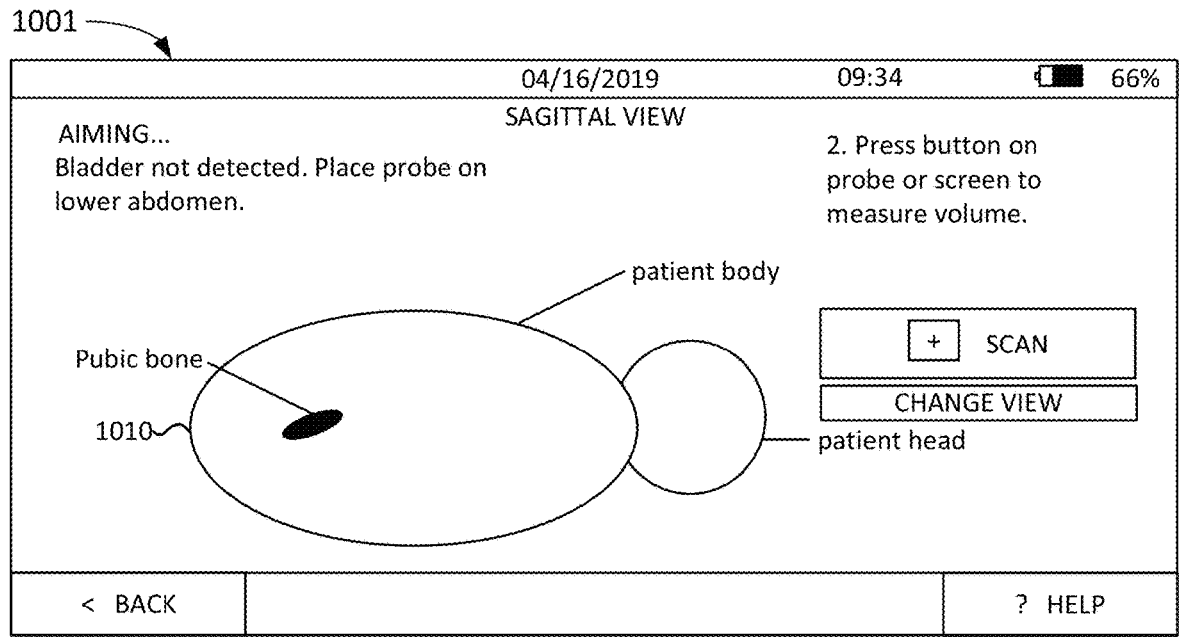
FIGS. 10A-10D are diagrams of user interfaces according to a third implementation described herein.

The user may be able to switch the view between different planes. For example, the user may switch between a transverse plane view and a sagittal plane view. FIGS. 10A-10D are diagrams of user interfaces that illustrate a sagittal view of the patient's body and use the patient's body as the frame of reference. FIG. 10A illustrated a user interface 1001 that may be displayed to the user when ultrasound system 100 first enters the aiming mode. User interface 1001 may include a sagittal plane view 1010 of the patient's body. In the sagittal plane view, the pubic bone may be displayed and may be used by the user as a point of reference when aligning ultrasound probe 110.

Figure 10B:
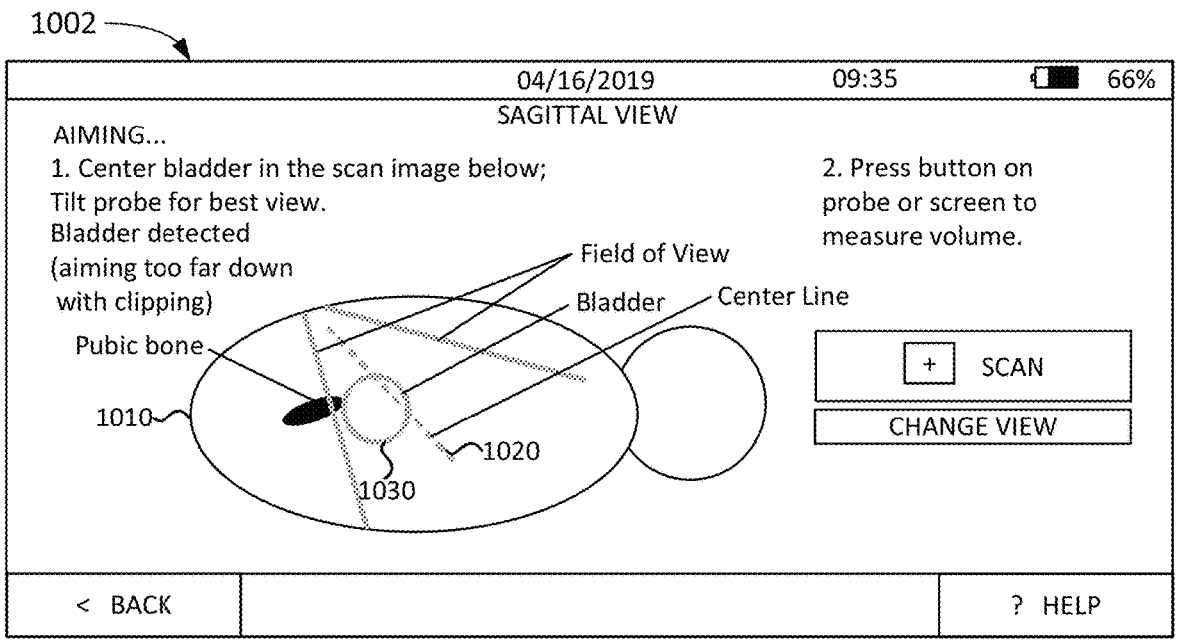

FIG. 10B illustrates user interface 1002 after the bladder is detected. User interface 1002 may include a field of view of ultrasound probe 110 with a center indicator 1020, displayed as the centerline of the field of view. Center indicator 1020 may initially be displayed in a red color. Furthermore, user interface 1002 may include an area indicator 1030, showing the patient's bladder as a red colored circle.

Figure 10C:
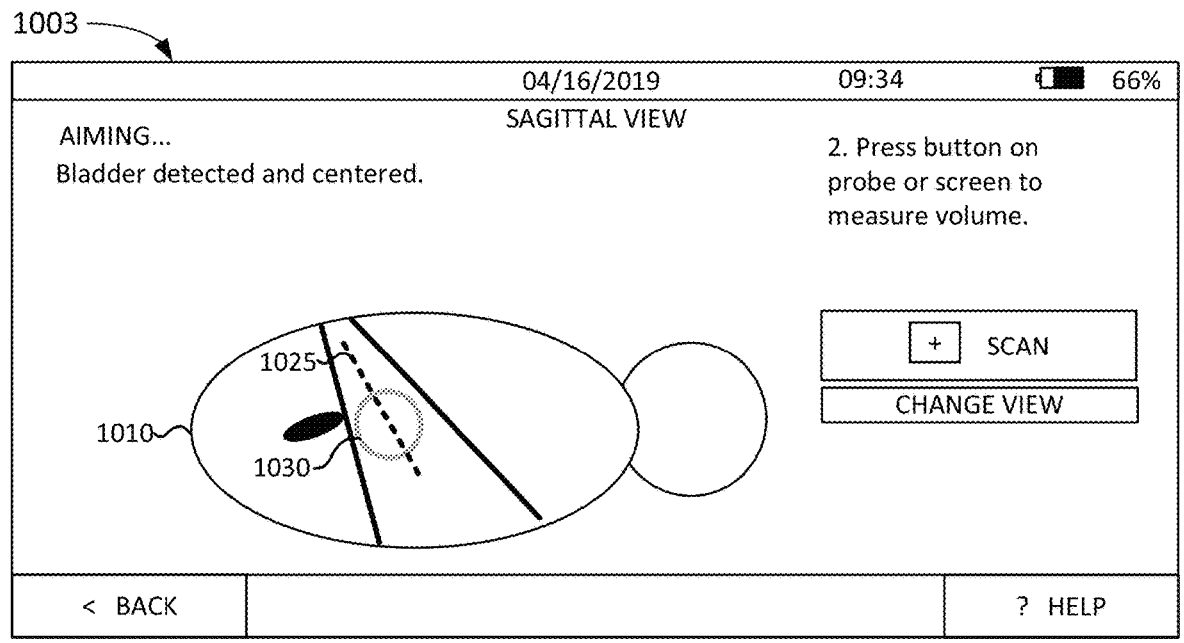

FIG. 10C illustrates user interface 1003 after ultrasound probe 110 has been centered. When the centroid of the detected bladder is determined to be within a particular number of pixels or distance of the centerline (e.g., within ten pixels, etc.), center indicator 1020 may be changed to highlighted center indicator 1025, such as by changing color from red to green. Furthermore, the field of view and highlighted center indicator 1025 may be shown as centered on the bladder, represented as area indicator 1030. During centering, the position of center indicator 1030 may change as ultrasound probe 110 is moved by the user to reflect the position of center indicator 1030 with respect to the bladder. The user may then be instructed to tilt ultrasound probe 110 in a particular direction (e.g., in a cranial-caudal direction) to identify the maximum cross-sectional area for the target.

Figure 10D:
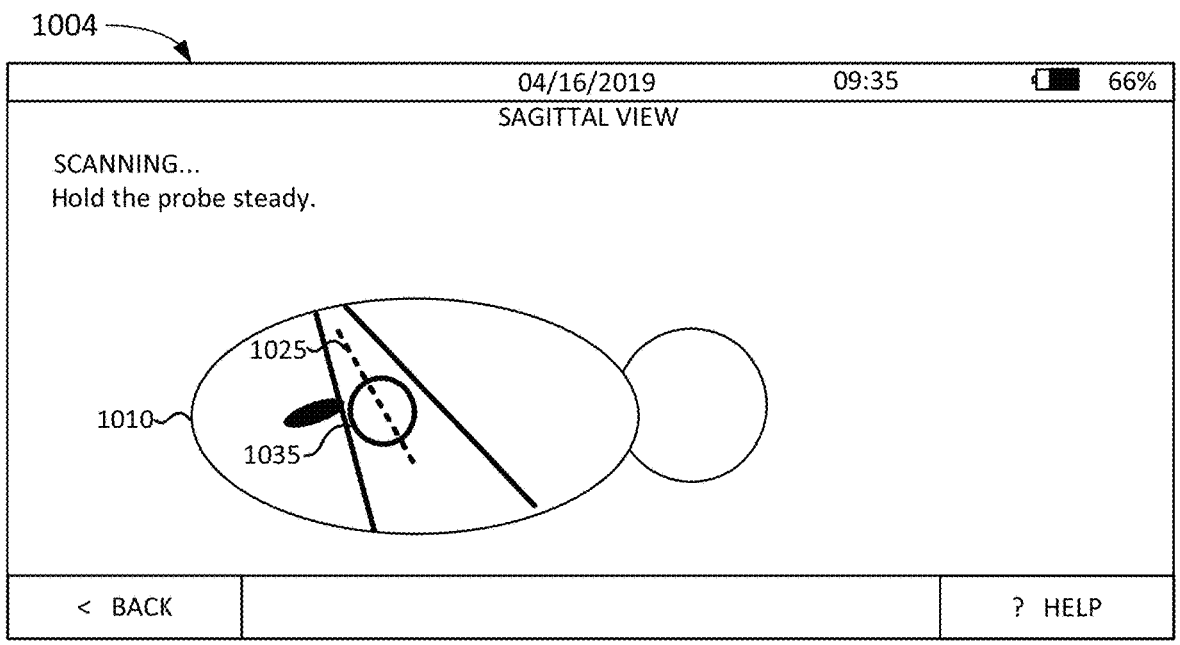

FIG. 10D illustrates user interface 1004 after the maximum cross-sectional area of the bladder has been identified and ultrasound probe 110 has been aligned to point at the maximum cross-sectional area. When ultrasound probe 110 is aligned to point at the maximum cross-sectional area of the bladder, area indicator 1030 may be changed to highlighted area indicator 1035. For example, the color of the circle representing the bladder may change from red to green. After ultrasound probe 110 has been held steady while being centered and pointing at the maximum cross-sectional area for a number of consecutive frame captures, such as ten frames (e.g., corresponding to a time of approximately two seconds), ultrasound system 100 may initiate the 3D scan of the bladder.

Figure 11A:
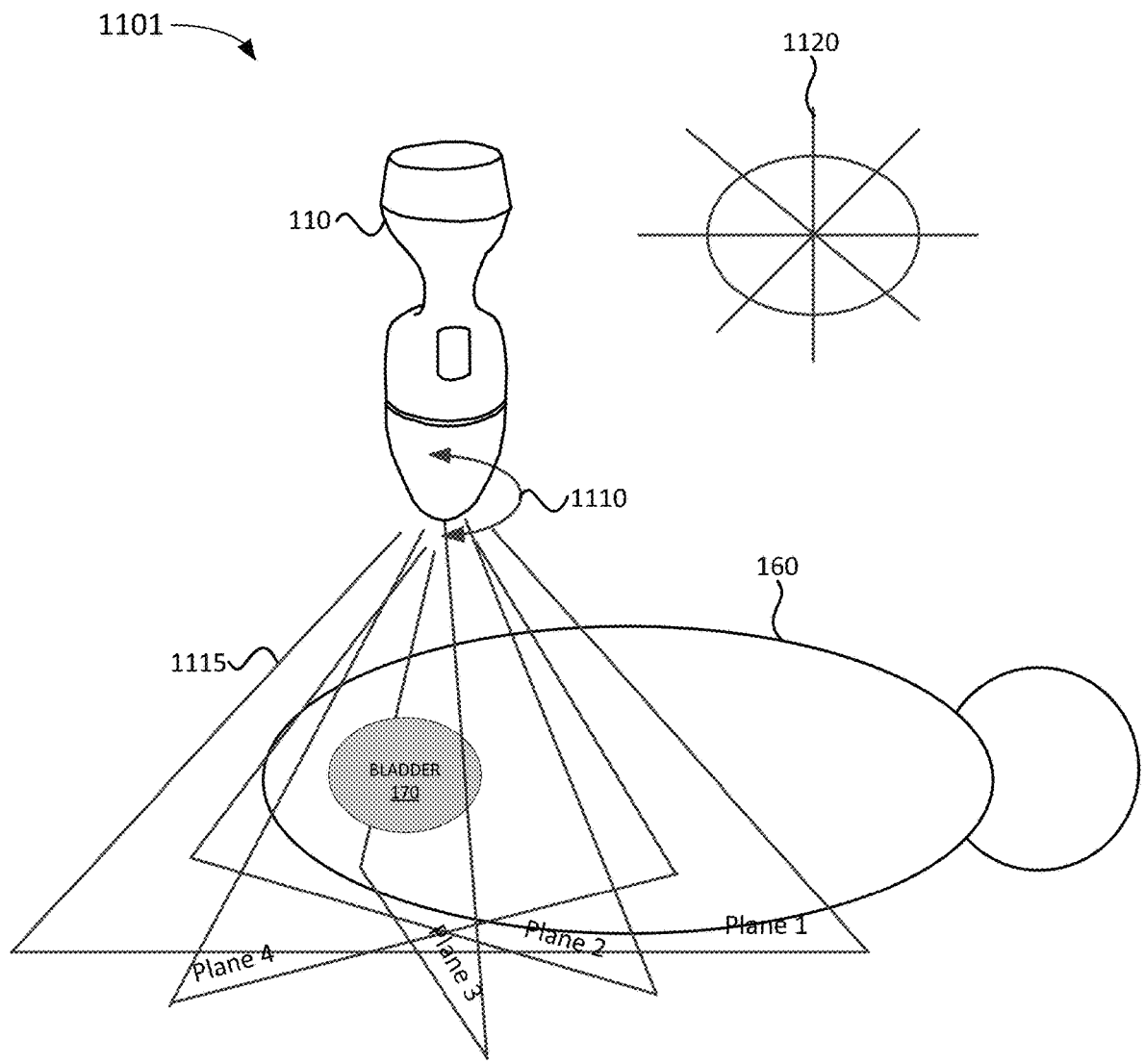
FIG. 11A is a diagram illustrating an aiming mode using a multi-plane scan according to an implementation described herein.

FIG. 11A illustrates an aiming mode 1101 that uses a multi-plane scan referred to as a C-mode. As shown in FIG. 11A, aiming mode 1101 may include ultrasound probe 110 performing a rotating motion 1110 back and forth around a vertical axis to perform B-mode scans in four planes 1115 separated by 45° to scan bladder 170 of patient 160. Top view 1120 illustrates the position of the scanning planes in the coronal plane. While four planes are shown in FIG. 11A, in other implementations, aiming mode 1101 may include a different number of planes. For example, aiming mode 1101 may include twelve planes separated by 15°.

Figure 11B:
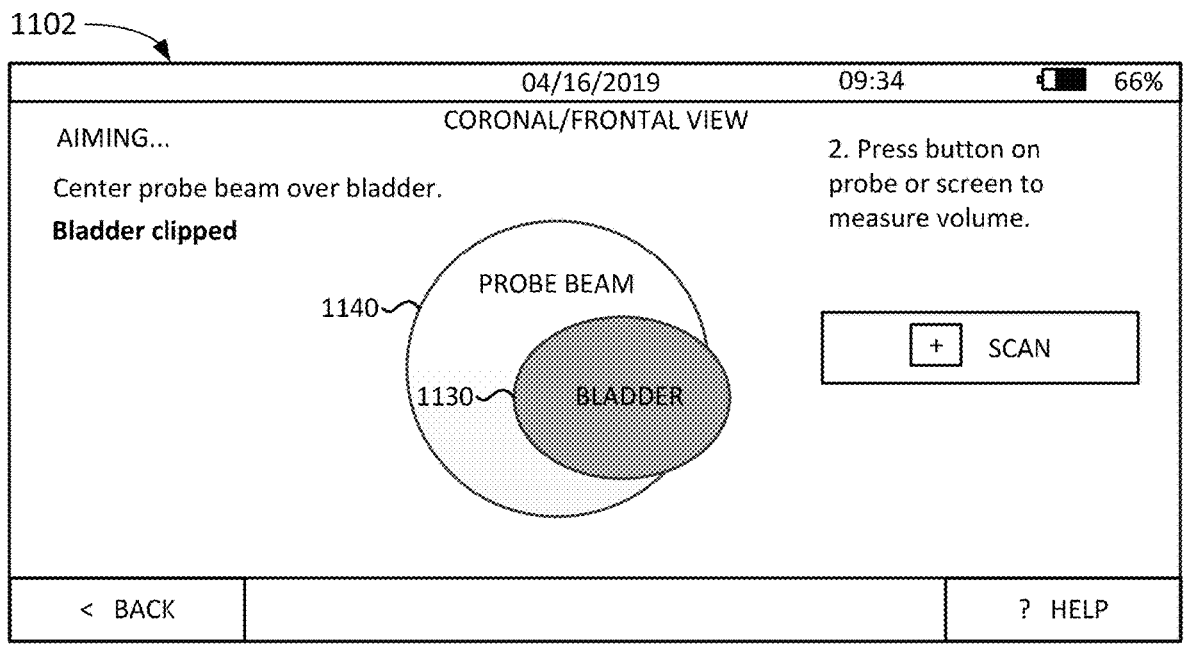
FIGS. 11B and 11C are diagrams of user interfaces associated with an aiming mode that uses a multi-plane scan.
Figure 11C:
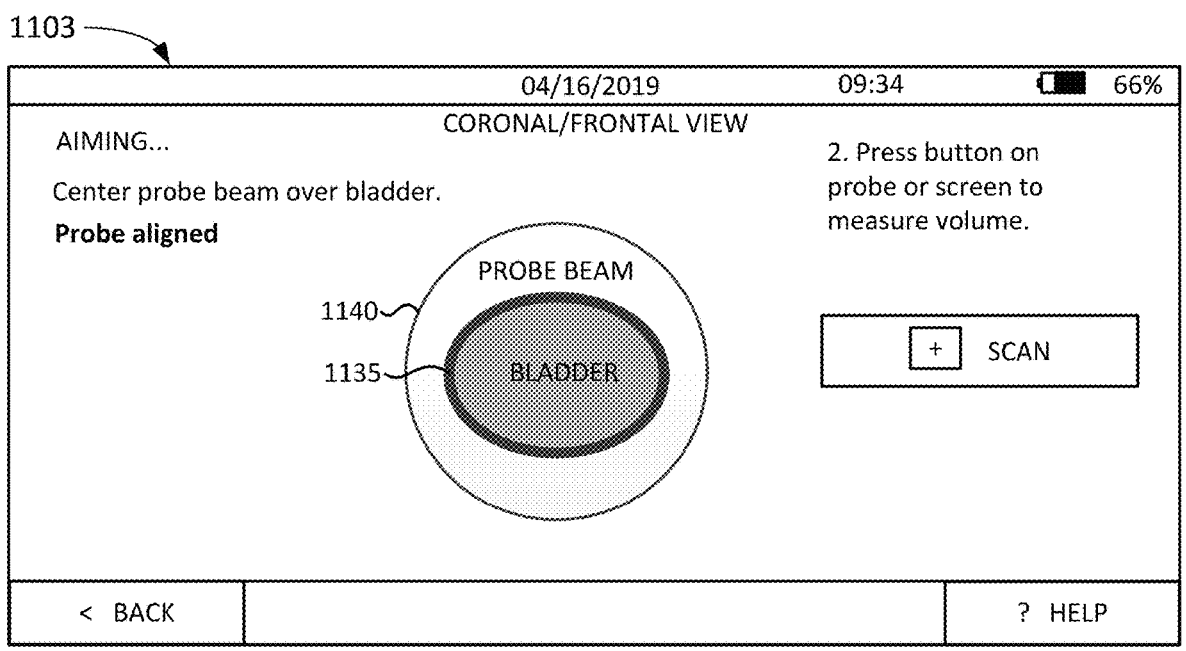

FIGS. 11B and 11C illustrate user interfaces 1102 and 1103 associated with aiming mode 1101. As shown in FIG. 11B, user interface 1102 may include a bladder representation 1130 and a beam representation 1140. Bladder representation 1130 may correspond to the determined location of bladder 170 of patient 160 after an initial aiming scan is performed using the four planes shown in FIG. 11A. Beam representation 1140 may correspond to a flashlight view of the field of view of ultrasound probe 110 in the current position of ultrasound probe 110 and may correspond to the cross-section of the ultrasound beam of ultrasound probe 110 in a plane that intersects bladder 170 (e.g., a plane that intersects bladder 170 at the maximum cross-section of bladder 170). The user may be provided with information to improve the aiming of ultrasound probe 110. For example, in FIG. 11B, part of bladder representation 1130 may fall outside beam representation 1140, indicating clipping of the target. The user may be instructed to position ultrasound probe 110 to eliminate clipping of the target and to align ultrasound probe 110 so that the target is position in the middle of the field of view of ultrasound probe 110.

As shown in FIG. 11C, user interface 1103 includes a highlighted bladder representation 1135 and beam representation 1140. Bladder representation 1130 may become highlighted bladder representation 1135 when bladder 170 is in the center of the field of view of ultrasound probe 110. For example, ultrasound system 100 may determine the centroid of bladder 170 and the center of the field of view of ultrasound probe 110 and determine that bladder 170 is in the center when the centroid is within a particular distance of the center of the field of view.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while series of blocks have been described with respect to FIG. 7, the order of the blocks may be modified in other implementations. Further, non-dependent blocks may be performed in parallel.

Although embodiments described above refer to scanning a bladder, other organs, joints, vessels, and/or body areas, such as an aorta, prostate, kidney, uterus, ovaries, aorta, heart, etc., could scanned and/or imaged in other implementations. For example, embodiments described above may be used to center an ultrasound probe during aiming in preparation for scanning an aorta to detect the presence of an aortic aneurysm.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a computing device, the method comprising:
    selecting, by the computing device, an aiming mode for an ultrasound probe;
    detecting, by the computing device, a target of interest in a patient's body based on an ultrasound image of the target of interest generated using the ultrasound probe;
    displaying, by the computing device, a symbolic or pictographic representation of at least one of the patient's body, a field of view of the ultrasound probe, or a beam of the ultrasound probe on a user interface displayed on a display device associated with the computing device, wherein the user interface does not display the ultrasound image while the aiming mode is selected and the symbolic or pictographic representation of the at least one of the patient's body, the field of view of the ultrasound probe, or the beam of the ultrasound probe is displayed;
    displaying, by the computing device, a symbolic or pictographic representation of the target of interest on the user interface in connection with the symbolic or pictographic representation of the at least one of the patient's body, the field of view of the ultrasound probe, or the beam of the ultrasound probe, wherein the user interface does not display the ultrasound image while the aiming mode is selected and the symbolic or pictographic representation of the target of interest is displayed;
    determining, by the computing device, a centroid for the detected target of interest based on the ultrasound image of the target of interest;
    displaying, by the computing device and on the display device, a center indicator at a position corresponding to the determined centroid on the symbolic or pictographic representation of the target of interest;
    detecting, by the computing device, that the center indicator is within a threshold number of pixels or distance of a centerline of the field of view of the ultrasound probe; and
    highlighting, by the computing device and on the display device, the displayed center indicator, in response to detecting that the center indicator is within the threshold number of pixels or distance of the centerline.

2. The method of claim 1, wherein displaying the symbolic or pictographic representation of the target of interest includes:
    displaying an area indicator for the target of interest.

3. The method of claim 2, further comprising:
    determining an area for the detected target of interest; and
    tracking the area for the detected target of interest, wherein the displayed area indicator does not change in size as the tracked area for the detected target of interest changes.

4. The method of claim 2, further comprising:
    tracking the area for the detected target of interest to determine a current area;
    determining that the current area corresponds to a maximum area; and
    highlighting the displayed area indicator, in response to determining that the current area corresponds to the maximum area.

5. The method of claim 4, wherein determining that the current area corresponds to the maximum area is based on the determined current area increasing and decreasing a particular number of times.

6. The method of claim 4, further comprising:
    determining that the ultrasound probe has remained centered and positioned pointing at the maximum area for at least a particular time period; and
    exiting the aiming mode and initiating a scan of the target of interest, in response to determining that the ultrasound probe has remained centered and positioned pointing at the maximum area for at least the particular time period.

7. The method of claim 1, wherein detecting the target of interest includes:
    using a neural network to identify boundaries of the target of interest.

8. The method of claim 7, wherein determining the centroid for the detected target of interest includes:
representing the boundaries as a polygon with a plurality of vertices; and
computing the centroid based on a center between a left-most vertex and a right-most vertex of the plurality of vertices.

9. The method of claim 1, wherein displaying the symbolic or pictographic representation of the at least one of the patient's body, the field of view of the ultrasound probe, or the beam of the ultrasound probe on the user interface includes: displaying a symbolic or pictographic representation of a B-mode field of view associated with the ultrasound probe, wherein a position of the ultrasound probe is stationary and wherein the center indicator is moved in the symbolic or pictographic representation of the B-mode field of view when the ultrasound probe is moved.

10. The method of claim 1, wherein displaying the symbolic or pictographic representation of the at least one of the patient's body, the field of view of the ultrasound probe, or the beam of the ultrasound probe on the user interface includes: displaying a symbolic or pictographic representation of a transverse view of the patient's body, wherein the center indicator is stationary and wherein the field of view of the ultrasound probe is moved when the ultrasound probe is moved.

11. The method of claim 1, wherein displaying the symbolic or pictographic representation of the at least one of the patient's body, the field of view of the ultrasound probe, or the beam of the ultrasound probe on the user interface includes: displaying a symbolic or pictographic representation of a sagittal view of the patient's body, wherein the center indicator is stationary and wherein the field of view of the ultrasound probe is moved when the ultrasound probe is moved.

12. A system comprising:
an ultrasound probe; and
a controller configured to:
select an aiming mode for an ultrasound probe;
detect a target of interest in a patient's body based on an ultrasound image of the target of interest generated using the ultrasound probe;
display a symbolic or pictographic representation of at least one of the patient's body, a field of view of the ultrasound probe, or a beam of the ultrasound probe on a user interface displayed on a display device associated with the controller, wherein the user interface does not display the ultrasound image while the aiming mode is selected and the symbolic or pictographic representation of the at least one of the patient's body, the field of view of the ultrasound probe, or the beam of the ultrasound probe is displayed;
display a symbolic or pictographic representation of the target of interest on the user interface in connection with the symbolic or pictographic representation of the at least one of the patient's body, the field of view of the ultrasound probe, or the beam of the ultrasound probe, wherein the user interface does not display the ultrasound image while the aiming mode is selected and the symbolic or pictographic representation of the target of interest is displayed;
determine a centroid for the detected target of interest based on the ultrasound image of the target of interest;
display, on the display device, a center indicator at a position corresponding to the determined centroid on the symbolic or pictographic representation of the target of interest;
detect that the center indicator is within a threshold number of pixels or distance of a centerline of the field of view of the ultrasound probe; and
highlight, on the display device, the displayed center indicator, in response to detecting that the center indicator is within the threshold number of pixels or distance of the centerline.

13. The system of claim 12, wherein, when displaying the symbolic or pictographic representation of the target of interest, the controller is further configured to:
display an area indicator for the target of interest.

14. The system of claim 13, wherein the controller is further configured to:
determine an area for the detected target of interest; and
track the area for the detected target of interest, wherein the displayed area indicator does not change in size as the tracked area for the detected target of interest changes.

15. The system of claim 13, wherein the controller is further configured to:
track the area for the detected target of interest to determine a current area;
determine that the current area corresponds to a maximum area; and
highlight the displayed area indicator, in response to determining that the current area corresponds to the maximum area.

16. The system of claim 15, wherein the controller is configured to determine that the current area corresponds to the maximum area based on the determined current area increasing and decreasing a particular number of times.

17. The system of claim 15, wherein the controller is further configured to:
determine that the ultrasound probe has remained centered and positioned pointing at the maximum area for at least a particular time period; and
exit the aiming mode and initiate a scan of the target of interest, in response to determining that the ultrasound probe has remained centered and positioned pointing at the maximum area for at least the particular time period.

18. The system of claim 12, wherein when detecting the target of interest, the controller is further configured to:
use a neural network to identify boundaries of the target of interest.

19. The system of claim 18, wherein, when determining the centroid for the detected target of interest, the controller is further configured to:
represent the boundaries as a polygon with a plurality of vertices; and
compute the centroid based on a center between a left-most vertex and a right-most vertex of the plurality of vertices.

20. The system of claim 12, wherein, when displaying the symbolic or pictographic representation of the at least one of the patient's body, the field of view of the ultrasound probe, or the beam of the ultrasound probe, the controller is configured to:
display a symbolic or pictographic representation of a B-mode field of view associated with the ultrasound probe, wherein a position of the ultrasound probe is stationary and wherein the center indicator is moved in the symbolic or pictographic representation of the B-mode field of view when the ultrasound probe is moved.

21. The system of claim 12, wherein, when displaying the symbolic or pictographic representation of the at least one of the patient's body, the field of view of the ultrasound probe, or the beam of the ultrasound probe, the controller is configured to: display a symbolic or pictographic representation of a transverse view of the patient's body, wherein the center indicator is stationary and wherein the field of view of the ultrasound probe is moved when the ultrasound probe is moved.

22. The system of claim 12, wherein, when displaying the symbolic or pictographic representation of the at least one of the patient's body, the field of view of the ultrasound probe, or the beam of the ultrasound probe, the controller is configured to: display a symbolic or pictographic representation of a sagittal view of the patient's body, wherein the center indicator is stationary and wherein the field of view of the ultrasound probe is moved when the ultrasound probe is moved.

23. A device comprising:
a processor configured to:
select an aiming mode for an ultrasound probe;
detect a target of interest in a patient's body based on an ultrasound image of the target of interest generated using the ultrasound probe;
display a symbolic or pictographic representation of at least one of the patient's body, a field of view of the ultrasound probe, or a beam of the ultrasound probe on a user interface displayed on a display device associated with the device, wherein the user interface does not display the ultrasound image while the aiming mode is selected and the symbolic or pictographic representation of the at least one of the patient's body, the field of view of the ultrasound probe, or the beam of the ultrasound probe is displayed;
display a symbolic or pictographic representation of the target of interest on the user interface in connection with the symbolic or pictographic representation of the at least one of the patient's body, the field of view of the ultrasound probe, or the beam of the ultrasound probe, wherein the user interface does not display the ultrasound image while the aiming mode is selected and the symbolic or pictographic representation of the target of interest is displayed;
determine a centroid for the detected target of interest based on the ultrasound image of the target of interest;
display, on the display device, a center indicator at a position corresponding to the determined centroid on the symbolic or pictographic representation of the target of interest;
detect that the center indicator is within a threshold number of pixels or distance of a centerline of the field of view of the ultrasound probe; and
highlight, on the display device, the displayed center indicator, in response to detecting that the center indicator is within the threshold number of pixels or distance of the centerline.

* * * * *